United States Patent
Attar et al.

(10) Patent No.: US 11,331,412 B2
(45) Date of Patent: *May 17, 2022

(54) CROSS-LINKED PROTEIN FOAMS AND METHODS OF USING THEREOF A POLYVALENT CELLULAR SCAFFOLD

(71) Applicant: BIO-CHANGE LTD., MP Carmel Beach (IL)

(72) Inventors: Ishay Attar, MP Carmel Beach (IL); Shay Yaacov Sherbo Zheli, Pardes Hanna (IL)

(73) Assignee: BIO-CHANGE LTD., MP Carmel Beach (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/652,636

(22) PCT Filed: Oct. 4, 2018

(86) PCT No.: PCT/IB2018/001239
§ 371 (c)(1),
(2) Date: Mar. 31, 2020

(87) PCT Pub. No.: WO2019/086952
PCT Pub. Date: May 9, 2019

(65) Prior Publication Data
US 2020/0237957 A1  Jul. 30, 2020

Related U.S. Application Data

(60) Provisional application No. 62/567,919, filed on Oct. 4, 2017.

(51) Int. Cl.
*A61L 27/22* (2006.01)
*A61L 27/24* (2006.01)
(Continued)

(52) U.S. Cl.
CPC ............ *A61L 27/222* (2013.01); *A61L 27/24* (2013.01); *A61L 27/26* (2013.01); *A61L 27/56* (2013.01); *A61L 2430/00* (2013.01)

(58) Field of Classification Search
CPC .... A61L 2400/06; A61L 27/222; A61L 27/38; A61L 27/24; A61L 27/26; A61L 27/56; A61L 2430/00
See application file for complete search history.

(56) References Cited

U.S. PATENT DOCUMENTS

| 4,530,905 A | 7/1985 | Freedman |
| 8,722,039 B2 | 5/2014 | Preiss-Bloom et al. |

(Continued)

FOREIGN PATENT DOCUMENTS

| AU | 2014201672 A1 | 4/2014 |
| WO | 2008076407 A2 | 6/2008 |

(Continued)

OTHER PUBLICATIONS

International Search Report to corresponding International Application No. PCT/IB2018/001239 dated Mar. 22, 2019 (2 pages).

(Continued)

*Primary Examiner* — Jianfeng Song
(74) *Attorney, Agent, or Firm* — Greenberg Traurig, LLP

(57) ABSTRACT

In one embodiment, the present invention provides a composition, wherein the composition is a porous scaffold, wherein the pores of the scaffold are from 1 to 500 microns, the composition comprising: a) a cross-linkable protein selected from the group consisting of collagen and gelatin; b) a cross-linker which induces cross-linking of the cross-linkable protein; and c) a liquid.

17 Claims, 10 Drawing Sheets

(51) Int. Cl.
   *A61L 27/56*   (2006.01)
   *A61L 27/26*   (2006.01)

(56) References Cited

U.S. PATENT DOCUMENTS

| | | | |
|---|---|---|---|
| 9,017,664 | B2 | 4/2015 | Preiss-Bloom et al. |
| 9,636,433 | B2 | 5/2017 | Iram et al. |
| 9,655,988 | B2 | 5/2017 | Iram et al. |
| 2003/0049299 | A1 | 3/2003 | Malaviya et al. |
| 2008/0213243 | A1 | 9/2008 | Preiss-Bloom et al. |
| 2010/0042144 | A1 | 2/2010 | Bennett |
| 2010/0063459 | A1 | 3/2010 | Preiss-Bloom et al. |
| 2011/0087271 | A1* | 4/2011 | Sargeant ............ A61B 17/0057 606/213 |
| 2011/0110882 | A1 | 5/2011 | Preiss-Bloom |
| 2011/0287068 | A1 | 11/2011 | Pitaru et al. |
| 2011/0112573 | A1 | 12/2011 | Bloom |
| 2012/0226211 | A1 | 9/2012 | Preiss-Bloom et al. |
| 2013/0131701 | A1 | 5/2013 | Komlos et al. |
| 2013/0157956 | A1 | 6/2013 | Kluijtmans et al. |
| 2014/0314732 | A1* | 10/2014 | Preiss-Bloom ........ A61K 47/02 424/94.2 |
| 2015/0196683 | A1 | 7/2015 | Iram et al. |
| 2015/0273103 | A1 | 10/2015 | Iram et al. |
| 2020/0016295 | A1 | 1/2020 | Tomer et al. |
| 2020/0222457 | A1 | 7/2020 | Attar |

FOREIGN PATENT DOCUMENTS

| | | |
|---|---|---|
| WO | 2012028863 A1 | 3/2012 |
| WO | 2016156992 A3 | 6/2016 |
| WO | 2016156992 A3 | 10/2016 |

OTHER PUBLICATIONS

International Search Report to corresponding International Application No. PCT/IB2016/000894 dated Oct. 21, 2016 (2 pages).
European Search Report to corresponding EP Application No. 16771468.2 dated Nov. 9, 2018.
Hellio et al., "Physically and Chemically Crosslinked Gelatin Gels," Macromolecular Symposia, vol. 241, No. 1, pp. 23-27 (2006).
Miao et al., "Physically crosslinked polyvinyl alcohol and gelatin interpenetrating polymer network thesta-gels for cartilage regeneration," Journal of Materials Chemistry B, pp. 9242-9249 (2015)/.
Supplementary European Search Report to corresponding EP Appln. No. 18873480.0 dated May 28, 2021 (9 pages).
Barbetta et al., "Enzymatic Cross-Linking versus Radical Polymerization in the Preparation of Gelatin PolyHIPEs and Their Performance as Scaffolds in the Culture of Hepatocytes," Biomacromolecules, vol. 7, pp. 3059-3068, 2006).

* cited by examiner

*Treated subdermal tissue at 90 days post injection*

*Non-treated (naïve) subdermal tissue at 90 days post injection*

10X magnification 40X magnification 15 days 30 days 90 days 150 days

CROSS-LINKED PROTEIN FOAMS AND METHODS OF USING THEREOF A POLYVALENT CELLULAR SCAFFOLD

CROSS REFERENCE TO RELATED APPLICATIONS

This application is a U.S. National Phase Application to International Application No. PCT/IB2018/001239, filed Oct. 4, 2018, which claims priority to U.S. Provisional Patent Application No. 62/567,919, filed on Oct. 4, 2017, the entire contents of each is incorporated by reference in its respective entirety.

FIELD OF THE INVENTION

The present invention relates to improved cross-linked compositions comprising a cross-linkable protein and a non-toxic material which induces cross-linking of the cross-linkable protein. The composition is intended for triggering biological processes of tissue regeneration.

BACKGROUND

Biomaterials that can form gels in situ are useful for a variety of applications, such as, for example, injectable matrices for controlled cell and/or drug delivery, injectable scaffolds for tissue engineering, or adhesives to bond tissue or seal gaseous or fluid leaks in a physiological environment.

SUMMARY

In one embodiment, the present invention provides a composition
wherein the composition is a porous scaffold,
wherein the pores of the scaffold are from 1 to 500 microns, the composition comprising:
a) a cross-linkable protein selected from the group consisting of collagen and gelatin;
b) a cross-linker which induces cross-linking of the cross-linkable protein; and
c) a liquid.
In one embodiment, the liquid is a physiological buffer.
In one embodiment, the composition is a foam.
In one embodiment, the cross-linkable protein is introduced into the composition as a micronized protein powder, having an average particle size between 5 to 200 microns.
In one embodiment, the cross-linkable protein comprises gelatin of 200 to 300 bloom.
In one embodiment, the cross-linkable gelatin is present in the composition in the range of 0.5% w/w to 25% w/w.
In one embodiment, the cross-linker is transglutaminase.
In one embodiment, the transglutaminase is present in the composition in the range of 0.0001% w/w to 2% w/w.
In one embodiment, the present invention provides a composition comprising:
a) cross-linkable gelatin;
b) a transglutaminase which induces cross-linking of the cross-linkable gelatin; and
c) a liquid,
wherein the composition is a porous scaffold, having a pore size from 1 to 500 microns,
wherein the cross-linkable gelatin is introduced into the composition as a micronized gelatin powder, having a particle size between 5 to 200 microns,
wherein the cross-linkable gelatin is of 200 to 300 bloom,
wherein the cross-linkable gelatin is present in the composition in the range of 0.5% w/w to %30 w/w, and
wherein the transglutaminase is present in the composition in the range of 0.0001% w/w to 2% w/w.
In one embodiment, the liquid is a physiological buffer.
In one embodiment, the composition is formed in situ in a patient at a site where the patient is in need of treatment of a tissue defect.
In one embodiment, the composition is formed prior to introducing the composition into a patient at a site where the patient is in need of treatment of a tissue defect.
In one embodiment, the present invention provides a method, wherein the methods treats a tissue defect or disease in a patient in need thereof, comprising:
a) introducing the composition into the patient at the site of the tissue defect, in an amount sufficient to treat the tissue defect or disease;
wherein the composition adheres to the tissue at the site of the defect.
In one embodiment, the present invention provides a method, wherein the methods treats a tissue defect or disease in a patient in need thereof, comprising:
a) forming the composition in the patient at the site of the tissue defect, in an amount sufficient to treat the tissue defect or disease;
wherein the composition adheres to the tissue at the site of the defect.
In one embodiment, the tissue defect is a wound.
In one embodiment, the tissue is impaired and in need of regeneration.
In one embodiment, the tissue defect is a bone defect.
In one embodiment, the composition induces regeneration of bone in the patient.
In one embodiment, at least one cell type infiltrates into and grows in the composition.
In one embodiment, the at least one cell type is a cell type from the group consisting of: pancreatic stem cells, enteroendocrine cells, osteocytes, hepatocyte, tenocytes, myocytes, hematocytes, chondrocytes, epithelial cells, endothelial cells, neurons, embryonic stem cells, mesenchymal stem cells, autologous marrow-derived mesenchymal stem cells, progenitor cells, hematopoietic stem cells, mesenchymal stem cells, neural stem cells, bone system stem cells, chondrocytes line stem cells, epithelial stem cells, and hepatic stem cells.
In one embodiment, the present invention provides a method, wherein the method stimulates fibroblasts to produce new collagen in a patient, comprising:
a) forming a composition in the patient in an amount sufficient to induce fibroblasts stimulation,
b) wherein the composition is configured to promote fibroblast stimulation and collagen synthesis, wherein the fibroblast attachment and collagen synthesis induce tissue (skin) rejuvenation, and
c) wherein the composition is a porous scaffold,
d) wherein the pores of the scaffold are from 1 to 500 microns, the composition comprising:
i. a cross-linkable protein selected from the group consisting of collagen and gelatin;
ii. a cross-linker which induces cross-linking of the cross-linkable protein; and
iii. a liquid.
In one embodiment, the gelatin is present in the composition in the range of 3% w/w to 30% w/w after dilution with a liquid.

In one embodiment, the gelatin is present in the composition in the range of 8% w/w to 25% w/w after dilution with a liquid.

In one embodiment, the gelatin is present in the composition in the range of 8% w/w to 20% w/w after dilution with a liquid.

DETAILED DESCRIPTION

Figure 1:
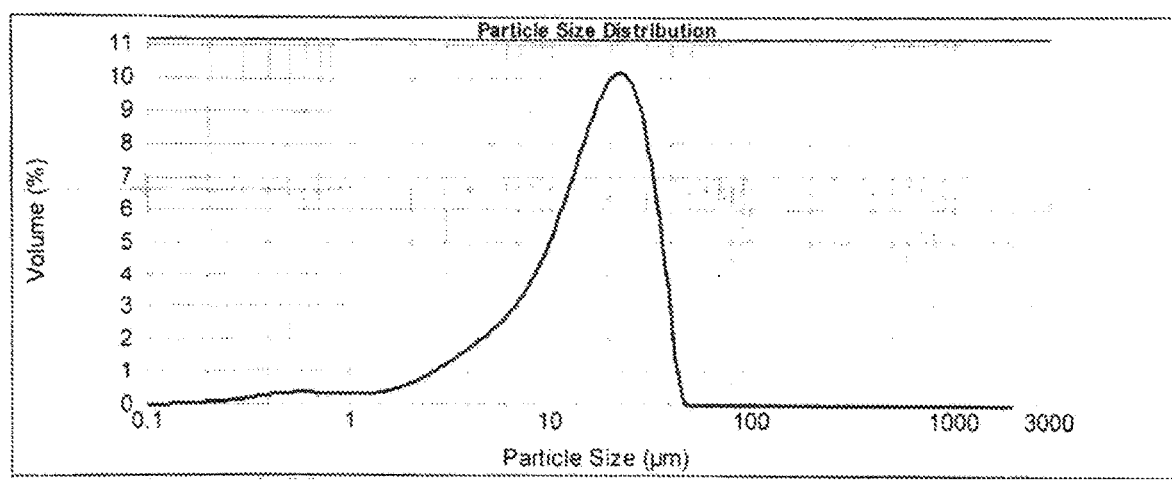
FIG. 1 is a graph showing the particle size distribution of the micronized protein according to some embodiments of the present invention.

For clarity of disclosure, and not by way of limitation, the detailed description of the invention is divided into the following subsections that describe or illustrate certain features, embodiments or applications of the present invention.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

"Gelatin" as used herein is obtained by partial hydrolysis of animal tissue or collagen obtained from animal tissue, wherein the animal tissue is selected from the group consisting of animal skin, connective tissue, antlers, horns, bones, fish scales, and a recombinant gelatin produced using bacterial, yeast, animal, insect, or plant systems (including, by non-limiting example, tobacco) or any type of cell culture, or any combination thereof.

"Bloom" as used herein is defined as the weight in grams required to impress a one-half inch diameter plunger 4 mm into a gelatin solution containing 6% solids gelled at 10 □C for 17 hours.

"Carrier" as used herein refers to a polymer, a protein, polysaccharide or any other constituent which binds the crosslinking enzyme covalently or non-covalently, either before or during the crosslinking reaction.

"Co-polymer" as used herein refers to a constituent of the matrix which can participate in the crosslinking reaction and is typically not the main constituent of the matrix. The co-polymer is typically not covalently bound to the enzyme or to the matrix material, such as the protein base of the matrix. Non-limiting examples of co-polymers are polysaccharides, such as dextran, and/or a cellulosic polymer, such as carboxymethyl cellulose.

"Cross-linking enzyme" as used herein refers to at least one enzyme (e.g., but not limited to, 1 enzyme, 2 enzymes, 3 enzymes, 4 enzymes, 5 enzymes, etc.) that can either directly (e.g., but not limited to, transglutamination) or indirectly (e.g., but not limited to, quinone or free radical formation) crosslink substrate groups on polymer strands to form a matrix, such as, but not limited to, a hydrogel.

"Diffusion" or "mobility" as used herein refers to the random molecular motion of, e.g., but not limited to, enzyme(s) and/or other molecules, e.g., but not limited to, any proteins, hydrogen, or matrix, that is/are in solution, which can result from Brownian motion.

"Diffusion coefficient" or "diffusivity" as defined herein refers to a term that quantifies the extent of diffusion for a single type of molecule under specific conditions. Specifically, diffusion coefficient or diffusivity is a proportionality, constant between the molar flux due to molecular diffusion and the gradient in the concentration of the species (or the driving force for diffusion). The method of measuring, i.e., the rate and/or the total amount of enzyme eluted by the hydrogel, is conducted by measuring the elution of enzyme from a hydrogel.

"Hydrodynamic volume" as defined herein refers to the molecular weight of a protein or enzyme that can typically be measured using size exclusion chromatography. The hydrodynamic volume of a constituent refers to the diameter and/or volume the constituent assumes when it is in motion in a liquid form.

"Matrix" as defined herein refers to a composition of cross-linked materials. Typically, when the matrix-forming materials are cross-linked, the composition that includes these materials transitions from a liquid state to a gel state, thereby forming a "gel," "hydrogel" or a "gelled composition."

"Molecular weight", abbreviated as "MW", as used herein refers to the absolute weight in Daltons or kilodaltons of proteins or polymers. For example, the MW of a PEGylated protein (e.g., but not limited to, protein to which one or more PEG (polyethylene glycol) molecules have been coupled) is the MW sum of all of its constituents.

"Patient", as used herein refers to any animal or human in need of treatment according to the methods of the present invention.

"Perceived volume" or "effective volume" as defined herein refers to the effective hydrodynamic volume of the crosslinking enzyme inside the cross-linked matrix. The perceived volume can be increased by covalent or non-covalent binding of the enzyme to another molecule, carrier, polymer, protein, polysaccharide and others, prior to the crosslinking reaction or during the crosslinking reaction.

"Polymer" as used herein refers to a natural, synthetic or semi-synthetic molecule, containing a repeatable unit.

"Reduced Mobility" as defined herein refers to a slower molecular motion or smaller diffusion coefficient of a protein or enzyme in a solution or inside a hydrogel and may be measured by the elution rate.

"Size" as defined herein refers to the molecular weight or hydrodynamic volume or perceived volume of a molecule.

"Milling" as defined herein refers to grinding the material by any of the following methods: jet milling, whirl/vortex milling, ball milling, high-pressure homogenization and microfluidization, spray drying, recrystallization, emulsion-solvent extraction and methods using supercritical fluids such as Rapid Expansion of Supercritical Solutions (RESS).

"Jet milling" refers to the method of micronization by whirl or vortex milling.

The Cross-Linkable Protein

According to at least some embodiments for the method and/or matrix, the at least one substrate polymer comprises a substrate polymer selected from the group consisting of a naturally cross-linkable polymer, a partially denatured polymer that is cross-linkable by the enzyme and a polymer comprising a functional group or a peptide that is cross-linkable by the non-modified or modified enzyme. Optionally the at least one substrate polymer comprises gelatin, collagen, casein or albumin, or a modified polymer, and wherein the modified enzyme molecule comprises a transglutaminase and/or an oxidative enzyme, a modified transglutaminase and/or a modified oxidative enzyme. Optionally the at least one substrate polymer comprises gelatin selected from the group consisting of gelatin obtained by partial hydrolysis of animal tissue or collagen obtained from animal tissue, wherein the animal tissue is selected from the group consisting of animal skin, connective tissue, antlers, horns, bones, fish scales, and a recombinant gelatin produced using bacterial, yeast, animal, insect, or plant systems or any type of cell culture, or any combination thereof. Optionally the gelatin is of mammalian or fish origin. Optionally the gelatin is of type A (Acid Treated) or of type B (Alkaline Treated). Optionally the gelatin is of 250-300 bloom. In some embodiments, gelatin has an average molecular weight of 75-150 kda.

In some embodiments, synthetic or partially synthetic polymers with one or more suitable functional groups could also serve as cross-linkable substrates for any of the enzymes described herein. In another embodiment of the present invention, a combination of enzymes is used. In another embodiment of the present invention, a combination of cross-linkers is used, not necessarily just an enzyme.

In some embodiments, the cross-linkable polymer contains at least one RGD (Arg-Gly-Asp) motif. In some embodiments, the at least one RGD motif promotes cell attachment to the composition of the present invention.

In some embodiments, the cross-linkable polymer contains an uneven distribution of RGD motifs which can act as a scaffold for cells, independent of the cell-type or motility state, making it a polyvalent cellular scaffold.

The present invention thus provides a cross-linkable polymer with improved cell attachment and motility compatibility through polyvalent display of RGD motifs.

The present invention thus provides a non-recombinant cross-linkable polypeptide with improved cell attachment and motility compatibility through polyvalent display of RGD motifs.

The present invention thus provides a gelatin with improved cell attachment and motility compatibility through polyvalent display of RGD motifs.

The present invention thus provides a non-recombinant gelatin with improved cell attachment and motility compatibility through polyvalent display of RGD motifs.

The present invention thus provides a micronized gelatin with improved cell attachment and motility compatibility through polyvalent display of RGD motifs The present invention thus provides a porous scaffold, such as a gelatin foam with improved cell attachment and motility compatibility through polyvalent display of RGD motifs The present invention thus provides a cross-linked porous scaffold, such as a gelatin foam with at least 3% w/w of gelatin, with improved cell attachment and motility compatibility through polyvalent display of RGD motifs.

The present invention thus provides a cross-linked porous scaffold, such as a gelatin foam with 105-25% w/w of gelatin, with improved cell attachment and motility compatibility through polyvalent display of RGD motifs.

The present invention thus provides any of the stated compositions with addition of fibrin.

"Polymer strands" or "polymer chains" as defined herein refers to the substrate polymer for enzyme crosslinking, which according to at least some embodiments of the present invention, belongs to one of the below categories (as non-limiting examples only):

1) Any polymer with substrate groups that are naturally cross-linkable by the enzyme and that is itself naturally cross-linkable by the enzyme. For example, in the case of transglutaminases, this would include protein or polypeptides such as gelatin, collagen, and casein which are naturally cross-linkable by the enzyme.

2) Polymers which contain substrate groups cross-linkable by the enzyme but which are not naturally cross-linkable by the enzyme as a result of their structure. In such cases, the polymer structure must be modified prior to enzyme crosslinking. For example, in the case of transglutaminases, this would include proteins, such as albumin or lactoglobulin, which are not natural substrates for the enzyme because they have a globular structure which hinders the access of the enzyme. These can be made into substrates by partially denaturing the protein using reducing agents, denaturing agents or heat.

3) Polymers, natural or synthetic, that are not substrates for enzyme crosslinking but that have been modified with peptides or functional groups which are substrates of the enzyme, thus rendering the modified polymer crosslinkable by the enzyme. Non-limiting examples of such polymers include any suitable type of protein, which may, for example, comprise gelatin as noted above. Gelatin may include any type of gelatin which comprises protein that is known in the art, including but not limited to, gelatin obtained by partial hydrolysis of animal tissue and/or collagen obtained from animal tissue, including but not limited to animal skin, connective tissue (including but not limited to ligaments, cartilage and the like), antlers or horns and the like, and/or bones, and/or fish scales and/or bones or other components; and/or a recombinant gelatin produced using bacterial, yeast, animal, insect, or plant systems or any type of cell culture, or any combination thereof.

According to some embodiments of the present invention, gelatin from animal origins can include gelatin from mammalian origins, e.g., but not limited to, one or more of pork skins, pork and cattle bones, or split cattle hides, or any other pig or bovine source, or any combination thereof. In some embodiments, the gelatin can include porcine gelatin since it has a lower rate of anaphylaxis. Gelatin from animal origins may optionally be of type A (Acid Treated) or of type B (Alkaline Treated), though it can be type A.

In some embodiments, gelatin from animal origins comprises gelatin obtained during a first extraction, which is generally performed at lower temperatures (50-60° C., although this exact temperature range is not necessarily a limitation). Gelatin produced in this manner will be in the range of 250-300 bloom and has a high molecular weight of at least about 95-100 kDa. In some embodiments, 275-300 bloom gelatin is used. A non-limiting example of a producer of such gelatins is PB Gelatins (Tessenderlo Group, Belgium).

According to some embodiments of the present invention, gelatin from animal origins can include gelatin from fish. In some embodiments, any type of fish may be used, for example, a cold water variety of fish such as carp, cod, or pike, or tuna. In some embodiments, the pH of fish gelatin (measured in a 10% w/w solution) can range from pH 4 to pH 6.

In some embodiments, cold water fish gelatin forms a solution in water at 10° C. In some embodiments, cold water fish gelatin is 0 bloom. In some embodiments, a high molecular weight cold water fish gelatin can be used, including an average molecular weight of at least about 95-115 kDa (where the cold water fish gelatin can be comparable to the molecular weight of a 250-300 bloom animal gelatin). In some embodiments, cold water fish gelatin undergoes thermoreversible gelation at lower temperatures than animal gelatin due to reduced amounts of proline and hydroxyproline. A non-limiting example of a producer of such a gelatin is Norland Products (Cranbury, N.J.).

In some embodiments of the present invention, low endotoxicity gelatin is used to form the gelatin solution component of the gelatin matrix composition. In some embodiments, low endotoxicity gelatin is available commercially from suppliers such as Gelita™ (Eberbach, Germany). As used herein, low endotoxicity gelatin is defined as gelatin with less than 1000 endotoxicity units (EU) per gram. In some embodiments, gelatin of endotoxicity less than 500 EU/gram is used.

In some embodiments, when generating materials that will come into contact with either the spine or the brain, gelatin with endotoxicity of less than 100 EU/gram is used (e.g., between 1-100 EU/gram). In some embodiments, gelatin with less than 50 EU/g is used. In some embodiments, gelatin with endotoxicity less than 10 EU/g can be used.

According to some embodiments of the present invention, type I, type II, or any other type of hydrolyzed or non-hydrolyzed collagen replaces gelatin as the protein matter being cross-linked. Various types of collagen have demonstrated the ability to form thermally stable mTG crosslinked gels. Such as, for example, as reported in publication "Characterization of a microbial transglutaminase cross-linked type II collagen scaffold"; PMID:16846344

According to some embodiments of the present invention, a recombinant human gelatin is used. In some embodiments, a recombinant human gelatin is available commercially from suppliers such as Fibrogen™ (San Francisco, Calif.). In some embodiments, a recombinant human gelatin is available commercially from suppliers such as Collplant Ltd. (Rehovot, Israel). In some embodiments, recombinant gelatin can be at least about 90% pure (e.g., 90.01-100%). In some embodiments, recombinant gelatin can be at least about 95% pure (e.g., 95.01-100%). In some embodiments, recombinant gelatins can be non-gelling at 10° C. and thus are considered to be 0 bloom. For some embodiments of the present invention, a high molecular weight recombinant gelatin can be used, for example, but not limited to, including a molecular weight of at least about 95-100 kDa.

In some embodiments, the cross-linkable protein can comprise gelatin but may also, additionally or alternatively, comprise another type of protein. According to some embodiments of the present invention, the protein is also a substrate for transglutaminase. In some embodiments, substrates for transglutaminase may include collagen or other synthesized polymer sequences that independently have the properties to form a bioadhesive or polymers that have been modified with transglutaminase-specific substrates that increase the ability of the material to be cross-linked by transglutaminase. The composition may also include fibrin.

In exemplary embodiments, synthesized polypeptide and polymer sequences with an appropriate transglutaminase target for cross-linking can have transition points from about 20 to about 40° C. In some embodiments, physical characteristics include but are not limited to the ability to bind tissue and the ability to form fibers. Non-limiting examples of such peptides are described in U.S. Pat. Nos. 5,428,014 and 5,939,385, which are hereby incorporated by reference as if fully set forth herein, describe biocompatible, bioadhesive, transglutaminase cross-linkable polypeptides wherein transglutaminase catalyzes an acyl-transfer reaction between the γ-carboxamide group of protein-bound glutaminyl residues and the c-amino group of Lys residues, resulting in the formation of 8-(y-glutamyl) lysine isopeptide bonds.

In some embodiments, the compound of the present invention is a substantially dry gelatin configured to rapidly hydrate with warm or cold liquids (e.g., but not limited to, liquids between 4° C. to 37° C.) to form a porous scaffold, gel or foam, where the porous scaffold, gel or foam is further configured to be shaped and molded into any cavity, ex-vivo or in-vivo, body cavity, on a wound, on an organ or any combination thereof. In some embodiments, the non cross-linked gelatin is reacted/mixed with the cross-linker after the non cross-linked gelatin and cross-linker are hydrated/reconstituted, where the mixing of the non cross-linked gelatin and cross-linker results in forming a stable, non-soluble, non-thermo reversible gel, foam or porous scaffold.

As used herein, the effect of the particle size on solubility constant can be quantified as follows:

$$\log(*K_A) = \log(*K_{A\rightarrow0}) + \gamma A_m / 3.454RT$$

where $*K_A$ is the solubility constant for the solute particles with the molar surface area A, $*K_{A\to 0}$ is the solubility constant for substance with molar surface area tending to zero (i.e., when the particles are large), γ is the surface tension of the solute particle in the solvent, Am is the molar surface area of the solute (in m²/mol), R is the universal gas constant, and T is the absolute temperature.

A typical technique for the preparation of micron-size particles of drugs and proteins is the mechanical commination (e.g., by crushing, grinding, and milling) of previously formed larger particles. In some embodiments of method of the present invention, the milling is achieved by mortar and in other preferred embodiment in Jet Milling. FIG. 1 illustrates particle size distribution after micronization by jet milling.

In some embodiments, the method of the present invention includes preparing a rapidly dissolving dry protein of non-crosslinked protein (e.g., but not limited to, gelatin). In some embodiments, the gelatin is prepared by jet milling to achieve a particle size between 2 to 250 microns. In some embodiments, the particle size is between 5 to 130 microns. In some embodiments, the particle size is between 10 to 80 microns. In some embodiments, the particle size is between 10 to 70 microns. In some embodiments, the particle size is between 10 to 60 microns. In some embodiments, the particle size is between 10 to 50 microns. In some embodiments, the particle size is between 10 to 40 microns. In some embodiments, the particle size is between 10 to 30 microns. In some embodiments, the particle size is between 10 to 20 microns. In some embodiments, the particle size is between 2 to 10 microns. In some embodiments, the particle size is between 10 to 100 microns. In some embodiments, the particle size is between 20-100 microns. In some embodiments, the particle size is between 30 to 100 microns. In some embodiments, the particle size is between 40 to 100 microns. In some embodiments, the particle size is between 50 to 100 microns. In some embodiments, the particle size is between 60 to 100 microns. In some embodiments, the particle size is between 70 to 100 microns. In some embodiments, the particle size is between 80 to 100 microns. In some embodiments, the particle size is between 90 to 100 microns. In some embodiments, the particle size is between 5 to 50 microns. In some embodiments, the particle size is between 10 to 20 microns. In some embodiments, the particle size is between 10 to 15 microns. In some embodiments, the particle size is between 15 to 20 microns. In some embodiments, the particle size is between 12 to 18 microns.

In some embodiments, the method of the present invention includes jet milling, where the jet milling results in preparing the surface of each gelatin particle (crystal) for rapid dissolving (e.g., but not limited to, dissolving in 0.01 second-60 seconds) in liquids (i.e., the resulting jet-milled particle surprisingly displays increased hygroscopic characteristics compared with non jet milled starting material). In some embodiments, the jet-milled particle can be mixed with a cross-linker to result in forming a thermally stable and tissue adherent hydrogel or foam. In some embodiments, the porous scaffold, gel/foam can be placed inside a body cavity and/or between tissue layers of a human or animal. In some embodiments, the present invention can be utilized for various medical applications. In some embodiments, the present invention can be utilized as a cellular scaffold presenting improved exposure and accessibility of integrin attachment sites (such as RGD motifs).

In some embodiments, a gelatin is prepared by milling into small particle size, to result in an increased cross-linking profile, where the prepared gelatin is characterized by having a micron size profile between 2-200 microns. In some embodiments, a gelatin is prepared by milling into small particle size, to result in an increased cross-linking profile, where the prepared gelatin is characterized by having a micron size profile between 2 to 100 microns. In some embodiments, a gelatin is prepared by milling into small particle size, to result in an increased cross-linking profile, where the prepared gelatin is characterized by having a micron size profile between 2 to 50 microns. In some embodiments, a gelatin is prepared by milling into small particle size, to result in an increased cross-linking profile, where the prepared gelatin is characterized by having a micron size profile between 50 to 150 microns. In some embodiments, a gelatin is prepared by milling into small particle size, to result in an increased cross-linking profile, where the prepared gelatin is characterized by having a micron size profile between 100 to 150 microns. In some embodiments, a gelatin is prepared by jet milling to result in an increased cross-linking profile, where the prepared gelatin is characterized by having a micron size profile. In some embodiments, the pre-crosslinked gelatin can be (1) lyophilized then (2) jet milled to produce a dry powdered gelatin (i.e., "high bloom gelatin"), where the dry powdered gelatin can solubilize in a solution to generate a solution in a temperature between, e.g., but not limited to, 5° C.-37° C., in a time period of equal to or less than 120 seconds (i.e., between 0.01 seconds-120 seconds).

Figure 9:
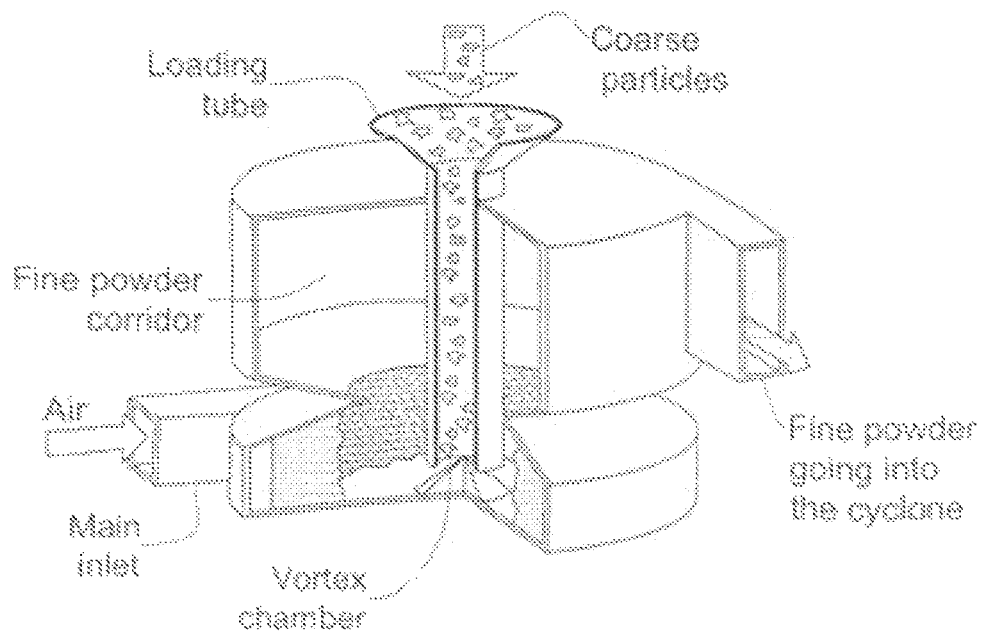
FIG. 9 is a photograph of a jet milling apparatus according to some embodiments of the present invention.
Figure 9:
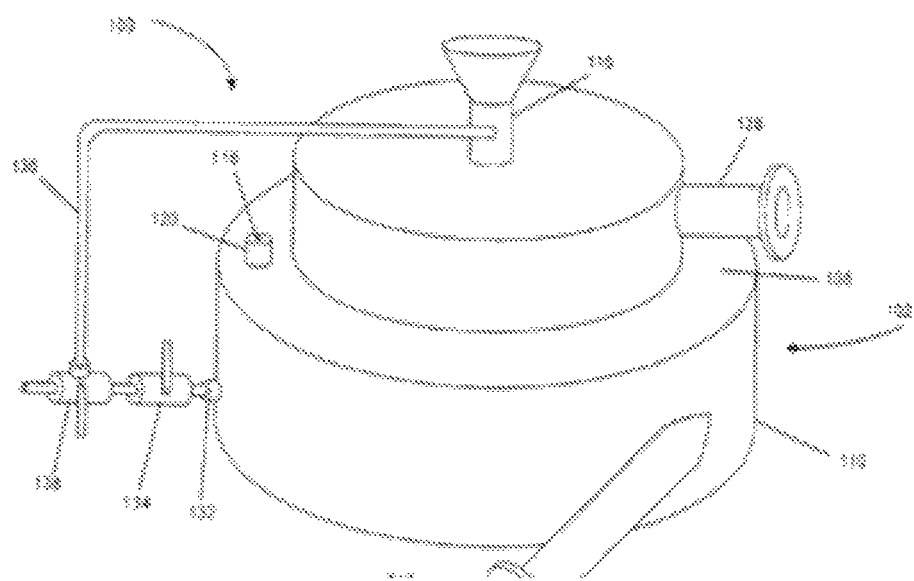

In one embodiment, the mill apparatus and method is as disclosed in U.S. Pat. No. 5,855,326, which is hereby incorporated in its entirety by reference. In another embodiment, the mill apparatus is as disclosed in U.S. Pat. No. 6,789,756, which is hereby incorporated in its entirety by reference. One example of such a milling apparatus is the SuperFine Vortex Mill™ manufactured by SuperFine Ltd. of Yokneam, Israel (shown schematically in FIG. 9). U.S. Pat. No. 5,855,326 to Beliaysky, whose entire contents are incorporated by reference, discloses a whirl milling chamber for fine comminution of a particulate solid material, the chamber being formed in a housing having a substantially cylindrical shape with two end faces and a side wall provided with one or more tangential nozzles for the injection of a working fluid into the chamber and creating a vortex therein, said chamber comprising means for the introduction there into a particulate solid material to be comminuted, an axially disposed discharge passage provided in one or both said end faces, and control means in the form of one or more mechanical elements adapted to interact, when the vortex is created, with its layers moving close to inner walls of the chamber, thereby enabling for control of the comminution. Operation of the whirl chamber is exemplified in the patent using sand. U.S. Pat. No. 6,789,756 to Beliaysky, whose entire contents are also incorporated by reference, discloses an improved vortex mill for milling a substantially particulate solid material, which includes one or more working chambers. The mill also includes one or more working fluid inlets and one or more discharge ports. One or more working fluid inlets together with one or more discharge ports facilitate the vortex flow within the one or more working chambers. There are also one or more feed inlets to provide milling of the solid material, which is discharged from one or more discharge ports. In addition, there is an apparatus for inducing controlled perturbations in the flow of the working fluid in the one or more working chambers, thereby to improve the milling of the solid material in the vortex flow.

In some embodiments, the method of the present invention can include using plasma beam energy for increasing the surface hygroscopy of the gelatin particles, where the resulting micronized gelatin treated with plasma beam energy has substantially the same characteristics/properties as the non-plasma beam treated gelatin. In some embodiments, additional substances/compounds for mixing with the gelatin, e.g., but not limited to, microbial transglutaminase, bone augmentation substances, protein and co-polymers to be mixed into the final product, or any combination thereof, can be treated with plasma beam energy.

In some embodiments, the composition of the present invention can be characterized as a hygroscopic particulate gelatin powder, when mixed with a liquid for a period of time between 0.01 to 120 seconds, is configured to solubilize into flowable gel or foam. In some embodiments, a liquid can be provided as part of the product formulation (i.e., a kit), loaded into syringe by a medical practitioner (e.g., a nurse, a physician, a physician's aide, etc.) at point of care, prior to the mixing. In some embodiments, the dry gelatin, alone or mixed together with a cross-linker, or both gelatin and cross-linker together with a surgical mesh can be applied directly to the body and be activated by applying fluids (i.e. saline) or by bodily fluids (i.e., liquids endogenous to a body) when in contact with moist tissue. In some embodiments, the milled gelatin powder can hydrate in temperatures of between 4 to 40° C. In some embodiments, the milled gelatin powder can hydrate in temperatures of between 4 to 20° C. In some embodiments, the milled gelatin powder can hydrate in temperatures of between 4 to 15° C. In some embodiments, the milled gelatin powder can hydrate in temperatures of between 10 to 25° C. In some embodiments, the milled gelatin powder can hydrate in temperatures of between 25 to 37° C. In some embodiments, the milled gelatin powder can hydrate in temperatures of between 15 to 25° C. In some embodiments, the milled gelatin powder can hydrate in temperatures of between 20 to 25° C. In some embodiments, the milled gelatin powder can hydrate in temperatures of between 10 to 20° C. In some embodiments, the milled gelatin powder can hydrate in temperatures of between 12 to 18° C. In some embodiments, the milled gelatin powder can hydrate in temperatures of between 14 to 19° C. (which is the range of temperature of an operating theater). In some embodiments, the milled gelatin powder can hydrate in temperatures of about 16° C. In some embodiments, the dissolved gelatin of the present invention is configured to maintain a flow-able form, even at temperatures lower than 37° C. (i.e., the dissolved gelatin will not immediately cross its liquid-gel transition point back to become a non-workable solid).

In some embodiments, the dissolved gelatin of the present invention can be delivered through a long needle, catheter or endoscope. In some embodiments, the dissolved gelatin of the present invention when foamed has lesser viscosity than a confluent gelatin hydrogel of the same composition.

In some embodiments, the method of the present invention includes preparing/sterilizing gelatin using a radiation energy, where the resulting radiated gelatin has substantially similar functional properties (e.g., ability to cross-link) compared with the non-radiated starting gelatin.

In some embodiments, the method of the present invention includes preparing/sterilizing gelatin using a radiation energy, where the resulting radiated gelatin has at least 25% of the functional properties (e.g., ability to cross-link) compared with the non-radiated starting gelatin. In some embodiments, the method of the present invention includes preparing/sterilizing gelatin using a radiation energy, the resulting radiated gelatin has between 25 to 100% of the functional properties (e.g., ability to be cross-linked) compared with the non-radiated starting gelatin.

In some embodiments, the method of the present invention includes mixing a gelatin powder with additional active components, e.g., but not limited to, stabilizers (e.g., but not limited to: EDC (1-Ethyl-3-(3-dimethylaminopropyl)-carbodiimide), NHS (N-hydroxysuccinimide), carbamide, glutaraldehyde, horseradish peroxidase and/or transglutaminase), where the mixed gelatin and stabilizer forms a stable porous scaffold, gel or foam, where the shape of the porous scaffold, gel or foam is non-reversible (i.e., due to covalent bonding cross-links between gelatin molecules). In some embodiments, cross-linking of the gelatin porous scaffold, gel or foam (i.e., stabilization) can occur outside or inside the body of the human or animal.

In some embodiments, the method of the present invention includes drying a polymer such as a protein and/or a polypeptide, where the protein and/or polypeptide is a collagen and/or gelatin and/or any gelatin variant, so as to result in a dry polymer having a substantially faster (e.g., but not limited to, 0.01 second to 60 seconds reconstitution) reconstitution profile in liquids compared with typical non-pulverized gelatin, including in environments that are cold or room temperature liquids (e.g., but not limited to, liquids between 5° C. to 37° C.). In some non-limiting exemplary embodiments, a gelatin powder can be characterized as having (1) a substantially longer shelf life (e.g., between 1 month to 36 months) and (2) a substantially faster reconstitution/solubility. In some embodiments, the dry polymer is sterilized, and the sterilized dry polymer exhibits substantially similar biological function and dissolution/reconstitution characteristics compared with a substantially similar non-sterilized dry polymer. In some embodiments, the dry polymer is sterilized, and the sterilized dry polymer exhibits at least 25% of the biological function and dissolution/reconstitution characteristics compared with a substantially similar non-sterilized dry polymer. In some embodiments, the dry polymer is sterilized, and the sterilized dry polymer exhibits between 50% to 100% of the biological function and dissolution/reconstitution characteristics compared with a substantially similar non-sterilized dry polymer.

The Cross-Linker

In exemplary embodiments, non-limiting examples of direct crosslinking enzymes, which directly crosslink substrate groups on polymer strands, include transglutaminases and oxidative enzymes. Examples of transglutaminases include microbial transglutaminase (mTG), tissue transglutaminase (tTG), keratinocyte transglutaminase, epidermal transglutaminase prostate transglutaminase, neuronal transglutaminase, human transglutaminase, and Factor XIII In some embodiments, these enzymes can be from either natural or recombinant sources. In some embodiments, glutamine and lysine amino acids in the polymer strands are substrates for transglutaminase crosslinking.

In exemplary embodiments, non-limiting examples of oxidative enzymes are tyrosinase, laccase, peroxidase, or any combination thereof. In some embodiments, the oxidative enzymes crosslink polymers by quinone formation (tyrosinase) or free radical formation (laccase, peroxidase). The quinones and the free radicals then interact with each other or with other amino acids or phenolic acids to crosslink the polymers. In some embodiments, the crosslinkable substrates for the oxidative enzymes may be any proteins which contain tyrosine or other aromatic amino acids. In some embodiments, the substrates can be carbohydrates which contain phenolic acids, such as, but not limited to, ferulic acid. In some embodiments, the carbohydrates can be, but are not limited to, arabinoxylan or pectin.

According to some embodiments of the method of the present invention, transglutaminase solutions undergo one-stage or multiple-stage purification to perform one or more of 1) remove fermentation residue from the transglutaminase mixture; 2) concentrate the amount of active transglutaminase in a transglutaminase solution; 3) purify the transglutaminase solution from carrier proteins and/or carbohydrates; 4) lower the endotoxin level of the transglutaminase solution; 5) remove all microbes from the transglutaminase solution, effectively sterilizing the solution; all without wishing to be limited to a closed list, or any combination thereof.

According to some embodiments of the present invention, the transglutaminase can be a recombinant transglutaminase. Such non-binding example is an enzyme that is expressed in E. coli bacteria.

In some embodiments, the solution of cross-linking material is filtered prior to mixing with the cross-linkable protein or polypeptide. In some embodiments, the filtration process first uses coarse filtration, sometimes known as clarification, to remove large blocks of fermentation residue that will rapidly block finer filtration steps. Non-limiting examples of such coarse filtration is about 0.45 µm pore size filtration and about 0.65 µm pore size filtration. In some embodiments, the solution of cross-linking material is can be passed through a filter of pore size of below 0.22 µm, for example to reduce the bioburden of the material below 10 colony forming units (CFU) per gram and make it appropriate for medical use. In some embodiments, the bioburden is reduced to achieve a sterility assurance level (SAL) of less than about 10-2. In some embodiments, the bioburden is reduced to achieve a sterility assurance level (SAL) of less than about 10-3, where SAL is a term used in microbiology to describe the probability of a single unit being non-sterile after it has been subjected to a sterilization process.

According to another embodiment of the method of the present invention, tangential flow and/or hollow fiber ultrafiltration techniques are used, to purify the solution of cross-linking material by removal of carrier carbohydrates and proteins, and to concentrate the solution. Pore sizes for use with this invention are those with pore sizes smaller than the size of the components of the cross-linking composition. In some embodiments, the crosslinking material is mTG and the pore size is in the range of 10-50 kDa. In an embodiment, the crosslinking material is mTG and the pore sizes are in the range of 10-30 kDa. In some embodiments, non-binding commercial examples of such are Uniflux (GE), AKTA Pilot (GE) or AKTA Flux 6 (GE).

In some embodiments, one or more size exclusion chromatography steps is/are used to selectively separate the crosslinking material from surrounding substances (e.g., such as, but not limited to, Phenyl Sepharose FF column (2.6*10 cm, Pharmacia Biotech) or such as Sephacryl column (GE)). In some embodiments, one or more hydrophobic and/or hydrophilic interaction chromatography steps are used to selectively separate the crosslinking material from surrounding substances. In some embodiments, the crosslinking material is a protein and one or more ion exchange chromatography steps is used to bind the crosslinking protein, purifying it from the surrounding materials.

In some embodiments, the crosslinking protein is mTG and one or more cation exchange chromatography steps is/are used to purify the mTG. In some embodiments, the cation exchange resin is a sepharose resin.

In some embodiments, purification reduces the endotoxin level of the crosslinking material to less than 5 endotoxin units (EU) per gram. In some embodiments, purification reduces the endotoxin level of the crosslinking material between 0.001 and 5 endotoxin units (EU) per gram.

In some embodiments, the crosslinking agent is mTG and purification results in an mTG composition wherein the specific activity is greater than 20 enzyme units per milligram and greater than 25 units per milligram. In some embodiments, the crosslinking material is mTG and purification results in an mTG composition wherein the specific activity is between 10 enzyme units per milligram and 35 units per milligram. In some embodiments, the crosslinking material is mTG and purification results in electrophoretic purity of between 95% and 99.9%.

In some embodiments, an mTG purification process, as a non-limiting example, is described herein that purifies a food-grade mTG product to produce an mTG composition with specific activity greater than 24 enzyme units per milligram, greater than 95% electrophoretic purity, less than 5 endotoxin units per gram, and less than 10 CFU/g. An mTG purification process, as a non-limiting example, is described herein that purifies a food-grade mTG product to produce an mTG composition with specific activity between 25-35 enzyme units per milligram, between 95-99.9% electrophoretic purity, between 0.001 and 5 endotoxin units per gram, 0.001<10 CFU/g, or any combination thereof. In some embodiment the purified enzyme of the said specifications is subsequently lyophilized with or without additional carbohydrates or stabilizers and subsequently subjected to terminal sterilization by gamma or e-beam radiation. In some embodiments the specific activity after said terminal sterilization is 5-30 enzyme units per milligram. In some embodiments the specific activity after said terminal sterilization is 20-30 enzyme units per milligram. In some embodiments the specific activity after said terminal sterilization is 20-25 enzyme units per milligram.

In some embodiments, an mTG purification process, as a non-limiting example, is described in the publication "Purification and Characterization of Novel Transglutaminase from *Bacillus subtilis* Spores"; PMID: 11193401.

In some embodiments, after purification, the mTG can be dried or freeze dried and then particulated by (any type of) milling into 5 to 50 micron hygroscopic particles, in a method similar to that described herein. In some embodiments, after purification the mTG can be mixed with cellulose ether (HPMC) as stabilizing hydrocolloid or with trehalose.

In some embodiments, the transglutaminase can be mixed with maltodextrin. In some embodiments, the maltodextrin is a stabilizer.

In some embodiments, an enriched and/or purified enzyme can be stabilized by adding microparticles that include mTG and a stabilizing excipient, and further comprising additive material, e.g., a stabilizing agent that can aid in stabilizing during radiation (E.g., but not limited to, cellulose, sugars, maltodextrin, carotenoids, ascorbate, L-tyrosine). In some embodiments, a stabilizing excipient is a polyol, mannitol, sucrose, glycerol, lactose, glycine, or trehalose.

In some embodiments, the modified transglutaminase comprises modified microbial transglutaminase. In some embodiments, the polymer is modified to permit crosslinking by the modified microbial transglutaminase. In some embodiments, the modified oxidative enzyme comprises one or more of tyrosinase, laccase, peroxidase, or any combination thereof. In some embodiments, the matrix further comprises a carbohydrate comprising a phenolic acid for being cross-linked by the modified oxidative enzyme as the at least one substrate polymer. In some embodiments, the carbohydrate comprises one or more of arabinoxylan or pectin. In some embodiments, the enzyme molecule is modified through PEGylation and wherein the PEGylation provides immunogenic masking by masking the enzyme molecule from an immune system of a host animal receiving the matrix. In some embodiments, the host animal is human.

Compositions According to Some Embodiments of the Present Invention

In some embodiments, the present invention provides a composition
wherein the composition is a porous scaffold,
wherein the pores of the scaffold are from 1 to 500 microns, the composition comprising:
a) a cross-linkable protein selected from the group consisting of collagen and gelatin;
b) a cross-linker which induces cross-linking of the cross-linkable protein; and
c) a liquid.

As used herein, the term "scaffold" refers to materials that have been engineered to cause desirable cellular interactions to contribute to the formation of new functional tissues for medical purposes. Cells can be 'seeded' into these structures capable of supporting three-dimensional tissue formation. Scaffolds can mimic the native extracellular matrix of the native tissue, recapitulating the in vivo milieu and allowing cells to influence their own microenvironments. Scaffolds can serve for at least one of the following purposes:
1) Allow cell attachment and migration;
2) Deliver and retain cells and biochemical factors;
3) Enable diffusion of vital cell nutrients and expressed products; or
4) Exert certain mechanical and biological influences to modify the behavior of the cell phase.

In some embodiments, the liquid is a physiological buffer.

In some embodiments, the composition is a foam.

In some embodiments, the cross-linkable protein is introduced into the composition as a micronized protein powder, having an average particle size between 5 to 200 microns.

In some embodiments, the cross-linkable protein comprises gelatin of 200 to 300 bloom.

In some embodiments, the cross-linkable gelatin is present in the composition in the range of 0.5% w/w to 25% w/w.

In some embodiments, the cross-linker is transglutaminase.

In some embodiments, the transglutaminase is present in the composition in the range of 0.0001% w/w to 2% w/w.

In some embodiments, the present invention provides a composition comprising:
a) cross-linkable gelatin;
b) a transglutaminase which induces cross-linking of the cross-linkable gelatin; and
c) a liquid,
wherein the composition is a porous scaffold, having a pore size from 1 to 500 microns,
wherein the cross-linkable gelatin is introduced into the composition as a micronized gelatin powder, having a particle size between 1 to 200 microns,
wherein the cross-linkable gelatin is of 200 to 300 bloom,
wherein the cross-linkable gelatin is present in the composition in the range of 0.5% w/w to 25% w/w, and
wherein the transglutaminase is present in the composition in the range of 0.0001% w/w to 2% w/w.

In some embodiments, the liquid is a physiological buffer.

In some embodiments, the composition is formed in situ in a patient at a site where the patient is in need of treatment of a tissue defect.

In some embodiments, the composition is formed prior to introducing the composition into a patient at a site where the patient is in need of treatment of a tissue defect.

In some embodiments, the dried cross-linker is a transglutaminase enzyme. In some embodiments, the dried protein composition is gelatin. In some embodiments, the dry particulate protein does not require a stabilizer. In some embodiments, the powders composition dissolves into a flowable solution within less than 5 minutes. In some embodiments, the powders composition dissolves into a flowable solution within less than 5 minutes. In some embodiments, the powders composition dissolves into a flowable solution within less than 5 minutes in temperature lower than 37° C. In some embodiments, the powders composition dissolves into a flowable solution within less than 1 minute in temperature lower than 27° C. In some embodiments, the powders composition dissolves into a flowable solution within less than 1 minute in temperature lower than 20° C., which is the standard temperature of an operating room. In some embodiments, the gelatin composition is stored together with the cross-linker powder in a single compartment. In some embodiments, the gelatin powder and cross-linker are mixed with a liquid in a ratio of up to 10 ml to 1 gram gelatin. In some embodiments, the gelatin powder and cross-linker are mixed with a liquid in a ratio of up to 8 ml to 1 gram gelatin. In some embodiments, the gelatin powder and cross-linker are mixed with a liquid in a ratio of up to 6 ml to 1 gram gelatin. In some embodiments, the gelatin powder and cross-linker are mixed with a liquid in a ratio of up to 4 ml to 1 gram gelatin. In some embodiments, the gelatin powder and cross-linker are mixed with a liquid in a ratio of up to 2 ml to 1 gram gelatin. In some embodiments, the mixture of powders is pressed into an absorbable or non-absorbable pad to provide it mechanical backing. In some embodiments, the pad is non-woven oxidized cellulose. In some embodiments, the press is into a surgical mesh, degradable or not. In some embodiments, a concentration of gelatin composition is in the range of 0.5%-25% w/w. In some embodiments, a concentration of gelatin composition is in the range of 8-20% w/w. In some embodiments, the dry gelatin powder contains less than about 15% moisture. In some embodiments, the dry gelatin powder contains less than about 8% moisture. In some embodiments, the composition has a pH in a range of from about 6 to about 7. In some embodiments, the dry cross-linker powder contains less than about 15% moisture. In some embodiments, the dry cross-linker powder contains less than about 8% moisture. In some embodiments, the transglutaminase is calcium independent.

In some embodiments, the transglutaminase is microbial transglutaminase or recombinant transglutaminase. In some embodiments, a protein concentration of the transglutaminase is present in an amount from about 0.0001% to about 2% w/w of the composition. In some embodiments, the transglutaminase is present in an amount of from about 0.01% to about 1.35% w/w of the composition. In some embodiments, the concentration of transglutaminase is in the range of from about 1 to about 180 enzyme units (U/mL) of total composition.

In some embodiments, a ratio of enzyme composition to gelatin composition is about 1:1 to 1:5 v/v if the enzyme and the gelatin were in solution. In some embodiments, a ratio of purified enzyme composition to gelatin composition is about 1:100 to 1:500 w/w if the enzyme and the gelatin were in solid dry form.

In some embodiments, the gelatin is produced from animal origin, recombinant origin or a combination thereof. In some embodiments, the animal origin is selected from the group consisting of fish and mammals. In some embodiments, the gelatin is of type A (Acid Treated) or of type B (Alkaline Treated). In some embodiments, the gelatin comprises high molecular weight gelatin of at least about 250 bloom, or equivalent thereof. In some embodiments, the composition further comprises a surfactant. In some embodiments, the surfactant is selected from the group consisting of polysorbate 20 (Tween™ 20), polyoxyethyleneglycol dodecyl ether (Brij™ 35), polyoxyethylene-polyoxypropylene block copolymer (Pluronic™ F-68), sodium lauryl sulfate (SLS) or sodium dodecyl sulfate (SDS), sodium laureth sulfate or sodium lauryl ether sulfate (SLES), poloxamers or poloxamines, alkyl polyglucosides, fatty alcohols, fatty acid salts, cocamide monoethanolamine, cocamide diethanolamine, or any combination thereof. In some embodiments, the composition further comprises a plasticizer. In some embodiments, the plasticizer is selected from the group consisting of sorbitol, citric acid alkyl esters, glycerol, glycerol esters, phthalic acid alkyl esters, sebacic acid alkyl esters, sucrose esters, sorbitan esters, acetylated monoglycerides, glycerols, fatty acid esters, glycols, propylene glycol, lauric acid, sucrose, glyceryl triacetate, poloxamers, diethyl phthalate, mono- and di-glycerides of edible fats or oils, dibutyl phthalate, dibutyl sebacate, polysorbate, polyethylene glycols (PEG) 200 to 20,000, Carbowax polyethylene glycols, polyvinyl alcohol (PVA), gum arabic, guar gum, xanthan gum, Plasdone.® (polyvinylpyrrolidone), mannitol, and any combination thereof.

In some embodiments, the composition of the present invention is a cross-linkable composition, comprising a milled lyophilized gelatin composition and a dried transglutaminase composition, wherein the dried transglutaminase composition is dispersed thoroughly throughout the milled lyophilized gelatin composition.

In some embodiments, the composition of the present invention is a cross-linkable composition, comprising a gelatin and a cross-linker, wherein the crosslinker reacts with the gelatin once mixed to form a biodegradable stabilized porous scaffold. In some embodiments, the porous scaffold remains flexible for at least two weeks on a tissue. In some embodiments, the transglutaminase is a modified enzyme molecule, the modified enzyme molecule having a modification that alters a perceived volume of the enzyme molecules in the crosslinked matrix as the matrix is being formed through cross-linking of the polymer. In some embodiments, the gelatin has an endotoxin content of 1200 I.U./g or less. In some embodiments, the gelatin jet milled by using less than 10 bar pressure drop. In some embodiments, the gelatin jet milling is by using less than 5 bar pressure drop. In some embodiments, the gelatin jet milling is by using less than 5 m^3/min required air flow. In some embodiments, the gelatin jet milling is by using less than 2 m^3/min required air flow. In some embodiments, the composition further comprises barium, iodine, other radioopaque substances, or combinations thereof.

In some embodiments, the method of the present invention includes preparing/sterilizing gelatin and cross-linker composition using a radiation energy, where the resulting radiated composition has at least 25% of the functional properties (e.g., ability to cross-link, enzyme specific activity) compared with the non-radiated starting composition. In some embodiments, the method of the present invention includes preparing/sterilizing gelatin-crosslinker composition using a radiation energy, where the resulting radiated gelatin has between 25% to 100% of the functional properties (e.g., ability to cross-link) compared with the non-radiated starting composition.

In some embodiments, the method of the present invention includes preparing/sterilizing gelatin and crosslinker composition using a ethylene oxide, where the resulting treated composition has at least 25% of the functional properties (e.g., ability to cross-link) compared with the non-treated, non-sterile starting gelatin. In some embodiments, the method of the present invention includes preparing/sterilizing composition using a ethylene oxide, where the resulting treated composition has between 25-100% of the functional properties (e.g., ability to cross-link) compared with the non-treated, non-sterile starting composition.

In some embodiments, the composition of the present invention is used for at least one purpose selected from the group consisting of: a scaffold for cells, a tissue remodeling agent, a bulking agent, a dermal filler, a bone adhesive, a tissue filler, a composition to reduce lung volume, a surgical sealant, a bio-adhesive, a fistula repair composition, a hemostat, a surgical mesh, a composition for sustained release of bio-active agents.

In some embodiments, at least one cell type infiltrates into and grows in the composition.

In some embodiments, the at least one cell type is a cell type from the group consisting of: pancreatic stem cells, enteroendocrine cells, osteocytes, hepatocyte, tenocytes, myocytes, hematocytes, chondrocytes, epithelial cells, endothelial cells, neurons, embryonic stem cells, mesenchymal stem cells, autologous marrow-derived mesenchymal stem cells, progenitor cells, hematopoietic stem cells, mesenchymal stem cells, neural stem cells, bone system stem cells, chondrocytes line stem cells, epithelial stem cells, and hepatic stem cells.

In some embodiments, the composition isolates the infiltrated at least one cell type from the patient's immune system.

In some embodiments, the composition is a foam. Without intending to be limited to any particular theory, the porous scaffold, once cross-linked (for instance by the mTG) can remain stable in-vivo and induce tissue in-growth and regeneration. Alternatively, the porous scaffold can serve as a three-dimensional support scaffold for cells. The cross-linked porous scaffold has improved cell attachment and motility compatibility.

In some embodiments, the cross-linkable protein is mixed with a cross-linker. In some embodiments, the cross-linkable protein and the cross-linker are dry powders, and the dry powders are mixed, and then dissolved by a physiological liquid, buffer or cell supporting media. In some embodiments, the cross-linker cross-links the protein only when both the cross-linkable protein and the cross-linker are dissolved in the physiological buffer.

In some embodiments, the medical material of the present invention will typically, in addition to the components described above, including medium components necessary for the culture of cells, salt (buffer components). Moreover, it may further contain the urge regeneration agent (growth factor) tissue in transplant unit when implanted. Usable growth factors for example, fibroblast growth factor (FGF: acidic fibroblast growth factor (aFGF), basic fibroblast growth factor (bFGF), etc. keratinocyte growth factor (KGF)), epithelial cells growth factor (EGF), nerve growth factor (NGF), transforming growth factor (TGF), plateletderived growth factor (PDGF), vascular endothelial growth factor (VEGF), hepatocyte growth factor (HGF), bone morphogenetic protein (BMP: BMP-2, BMP-3, BMP-7, etc.) can be exemplified. These growth factors may be used by appropriate selection depending on the type of tissue for the purpose of reproduction. Specifically, for example, epidermal growth factor in the case of the purpose of regeneration of epidermal cells and in the case of the purpose of regeneration of the dermis it is possible to use each of the fibroblast growth factor. Specifically, for example, bone morphogenetic protein in the case of the purpose of regeneration of bone cells and in the case of the purpose of regeneration of the dermis it is possible to use each of the fibroblast growth factor. If it is preferable as it is being considered, it may be used in combination with growth factors of two or more kinds.

In some embodiments, dry powders can be packaged in a syringe or any container. In some embodiments, dry powders can be sterilized by radiation or ethylene oxide (ETO).

In some embodiments, the cross-linkable protein is mixed and the cross-linker are combined with at least one other agent selected from the group consisting of: stabilizers (e.g., but not limited to: EDC (1-Ethyl-3-(3-dimethylaminopropyl)-carbodiimide), NHS (N-hydroxysuccinimide), carbamide, glutaraldehyde, horseradish peroxidase, growth factors, therapeutic agents, and hormones.

Figure 2:
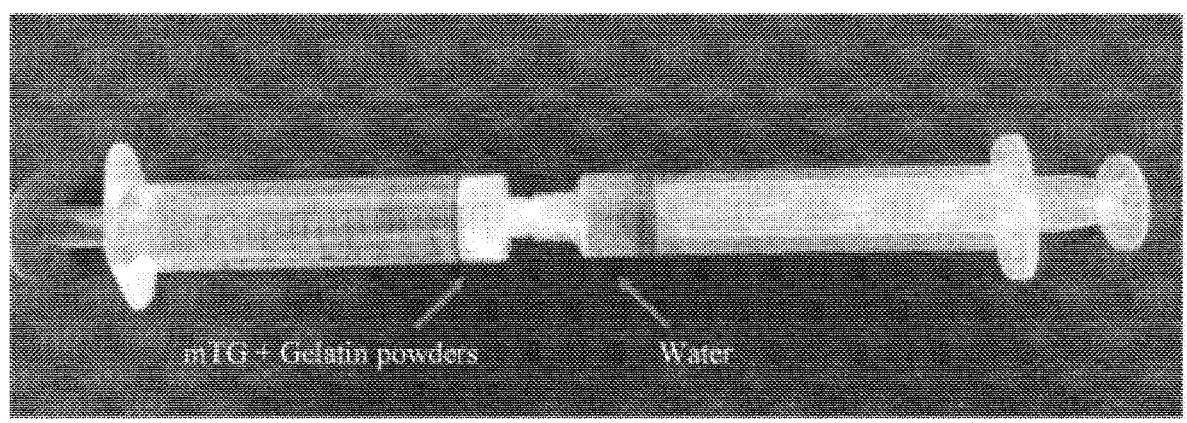
FIG. 2 is a photograph of a device according to some embodiments of the present invention for forming a composition of the present invention.
Figure 3A:
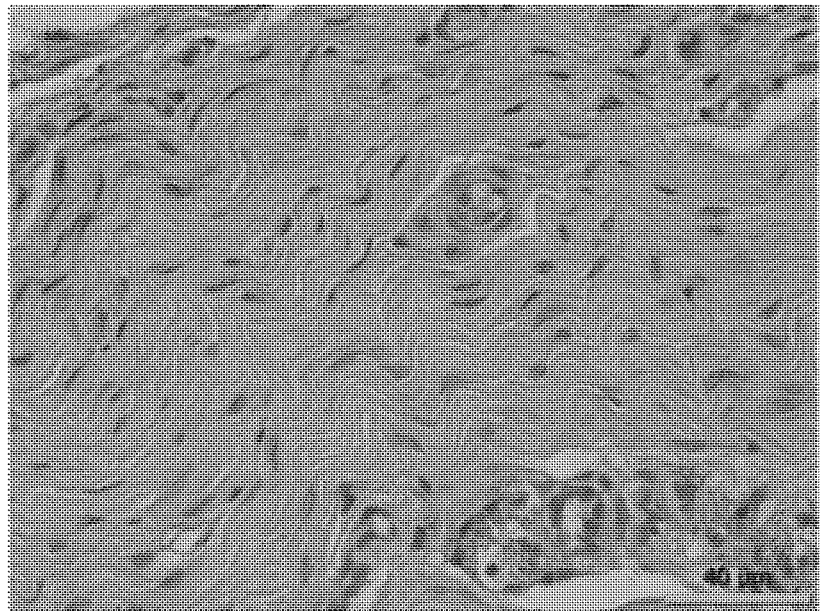
FIG. 3A is a photograph showing cells in treated tissue according to some embodiments of the present invention.
Figure 3B:
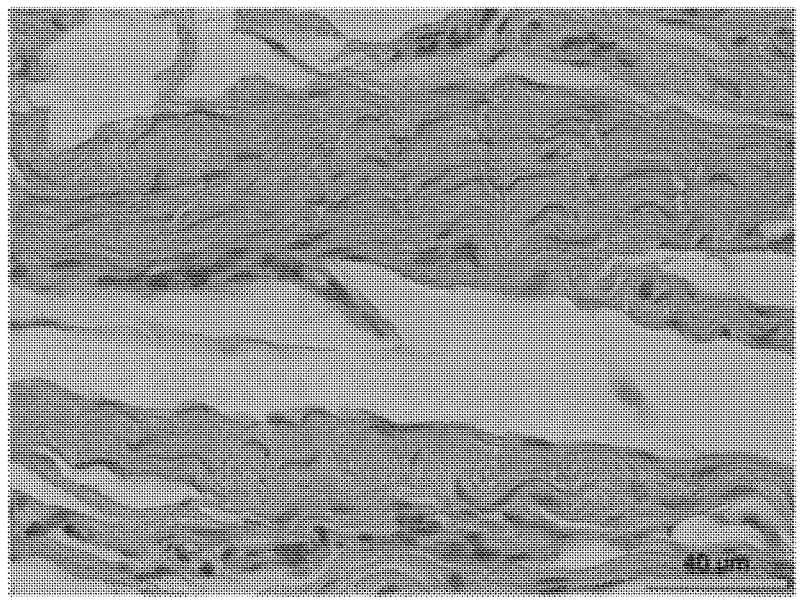
FIG. 3B is a photograph showing cells in non-treated tissue according to some embodiments of the present invention.

In some embodiments, the dry powders have reduced leaching and/or interactions when mixed as dry powders. Referring to FIG. 2, in some embodiments, the dry powders are dissolved in physiological buffer separately, and mixed by pushing the dissolved components from one interconnected syringe to another. However, any mixing method, such as stirring, may suffice. Alternatively, the dry powders are mixed together, and then the mixture is dissolved in the physiological buffer for activation.

In some embodiments, the cross-linking of the protein results in the porous scaffold. In some embodiments, the porous scaffold is thermostable. In some embodiments, the porous scaffold is adhesive. Without intending to be limited by any particular theory, the cross-linking is irreversible due to covalent bonds forming the cross-links between the protein molecules. In some embodiments, the porous scaffold is structurally similar to the extracellular matrix of mammalian tissues, can often be processed under mild conditions, and may be delivered in a minimally invasive manner.

The cross-linking can occur outside or inside the body of the patient. Thus, in some embodiments, the cross-linking occurs in situ at a site in the patient. Alternatively, the porous scaffold is formed ex-vivo then introduced into the patient.

In some embodiments, the hydrogel of the present invention, while not yet cured, can pass through the needle, once delivered in liquid form to the tissue; the adhesive stabilizes into a stable and consolidated physical formation (i.e., unified single particle of at least 0.05 ml volume).

The results of Example 4 indicate that by reducing particles size below d(0.5)=15 micron, the gelatin dissolves well but reacts slower with the microbial transglutaminase enzyme. In some embodiments of the invention, there is a need to provide rapidly dissolving powders that do not stabilize fast after hydration. They need to pass through a long needle and allow sufficiently long working time for the surgeon. In some embodiments such a formulation can be achieved with controlling gelatin particle size between 1-15 microns. In some embodiments such a formulation can be achieved with gelatin particle size between 8-14 microns.

In some embodiments, the composition comprises a porous scaffold configured to (1) stabilize in-situ or ex-vivo and (2) conform into a desired shape or body cavity, resulting in forming a biocompatible sealant or scaffold, configured to allow for ingrowth of cells and tissue.

In some embodiments, the stabilized porous scaffold structure is tissue conductive and can be used for the following medical uses: tissue remodeling agent, bulking agent, tissue fillers or tissue printing (such as 3D tissue printing). The pulverization of the gelatin and/or reconstitution into cross-linked porous scaffold (specifically by transglutaminase), greatly improves cell attachment and motility. Uneven and abundant display of integrin recognition motifs (such as RGD) on the gelatin porous scaffold and the accessibility of cells to such motifs, enhance its function as a scaffold.

In the embodiment of tissue printing, the dry powders can be applied through the printer in conjunction with living cells to compose a precise 2D or 3D structure of cells adhered to each other by the powdered or reconstituted glue. For example, by way of illustration, such 3D structures can contain some endothelial cells for forming blood vessels, that can be printed in the scaffold, with intention that they will provide blood supply to the inner cells, once the scaffold is implanted.

In some embodiments, the porous scaffold has a density, where the density is directly related to a degradation of the porous scaffold and/or cell ingrowth dynamics. In some embodiments, additional bioactive substances can also influence cell ingrowth dynamics (i.e., increase cell ingrowth dynamics) by, e.g., but not limited to, increase by 10% to 300%. In some embodiments, the suspended bio-active substances and/or cells and/or the Platelets Rich Plasma (PRP) and/or the growth factors and/or the bone morphogenetic proteins substantially remain in the target area of the body (e.g., but not limited to, without the patient having to keep the treated body area immobilized for an unreasonably long period or multiply injected with the factors, as normally practiced).

In some embodiments, the foam is initially a closed cell foam having an elasticity (Young's) modulus of between 0.1-11 KPa, where the elasticity modulus can be varied by changing concentrations of the protein, cross-linker, and/or physiological buffer and/or by changing the bloom of the gelatin used therein.

In some embodiments, the protein foam has an initial elasticity (Young's) modulus of between 1-11 KPa. In some embodiments, the protein foam has an initial elasticity (Young's) modulus of between 2-10 KPa. In some embodiments, the initial (i.e. about 30 minutes after crosslinking) elongation of the stabilized foam is between 0.1 to 1 times the original starting length. In some embodiments, the initial elongation of the stabilized foam is between 0.1 to 1.5 times the original starting length. In some embodiments, the initial elongation of the stabilized foam is between 0.1 to 2 times the original starting length. In some embodiments, the initial elongation of the stabilized foam is between 0.1 to 3 times the original starting length. In some embodiments, the initial elongation of the stabilized foam is between 0.1 to 4 times the original starting length. In some embodiments, the initial elongation of the stabilized foam is between 0.1 to 5 times the original starting length. In some embodiments, the initial elongation of the stabilized foam is between 1 to 2 times the original starting length. In some embodiments, the initial elongation of the stabilized foam is between 1 to 3 times the original starting length. In some embodiments, the initial elongation of the stabilized foam is between 1 to 4 times the original starting length. In some embodiments, the initial elongation of the stabilized foam is between 1 to 5 times the original starting length. In some embodiments, the initial elongation of the stabilized foam is between 1.5 to 2 times the original starting length. In some embodiments, the initial elongation of the stabilized foam is between 1.5 to 3 times the original starting length. In some embodiments, the initial elongation of the stabilized foam is between 1.5 to 4 times the original starting length. In some embodiments, the initial elongation of the stabilized foam is between 1.5 to 5 times the original starting length. In some embodiments, the initial elongation of the stabilized foam is between 2 to 3 times the original starting length. In some embodiments, the initial elongation of the stabilized foam is between 2 to 4 times the original starting length. In some embodiments, the initial elongation of the stabilized foam is between 2 to 5 times the original starting length. In some embodiments, the initial elongation of the stabilized foam is between 3 to 4 times the original starting length. In some embodiments, the initial elongation of the stabilized foam is between 3 to 5 times the original starting length.

An embodiment showing mechanical measurement of a foam comprising gelatin as the protein and mTG as the cross-linker is illustrated in tables of Example 5.

In some embodiments, the pore size of the porous scaffold is between 1 to 500 microns in diameter. In some embodiments, the pore size of the porous scaffold is between 2 to 400 microns in diameter. In some embodiments, the pore size of the porous scaffold is between 2 to 300 microns in diameter. In some embodiments, the pore size of the porous scaffold is between 2 to 200 microns in diameter.

In some embodiments, the pore size of the porous scaffold is between 2 to 50 microns in diameter. In some embodiments, the pore size of the porous scaffold is between 2 to 10 microns in diameter.

In some embodiments, the pore size of the porous scaffold is between 10 to 500 microns in diameter. In some embodiments, the pore size of the porous scaffold is between 50 to 400 microns in diameter. In some embodiments, the pore size of the porous scaffold is between 100 to 400 microns in diameter. In some embodiments, the pore size of the porous scaffold is between 200 to 400 microns in diameter. In some embodiments, the pore size of the porous scaffold is between 300 to 400 microns in diameter.

Figure 8:
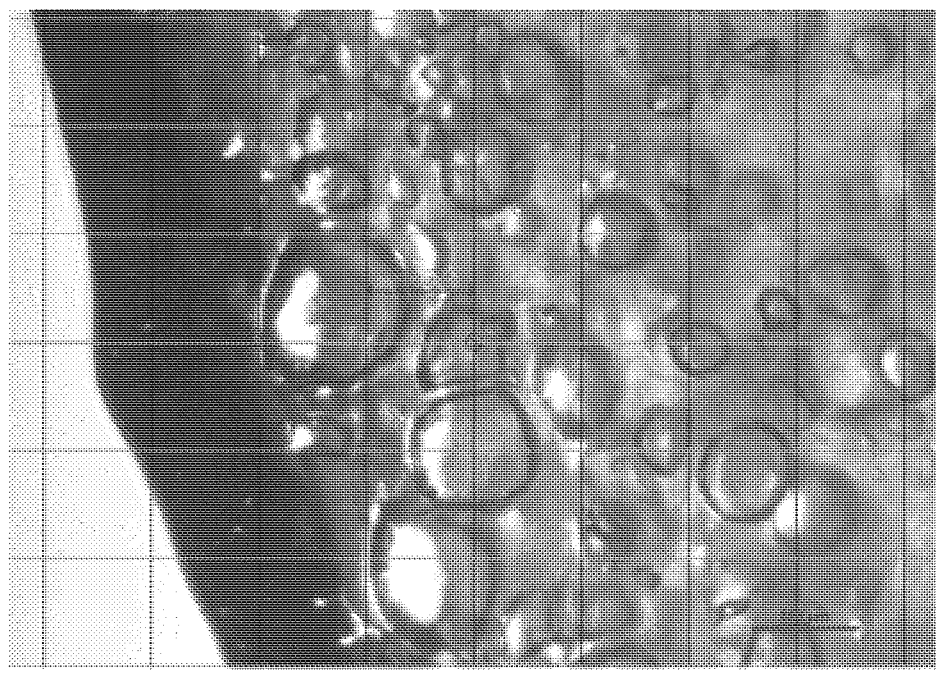
FIG. 8 is a micrograph of a composition according to some embodiments of the present invention.
Figure 8:
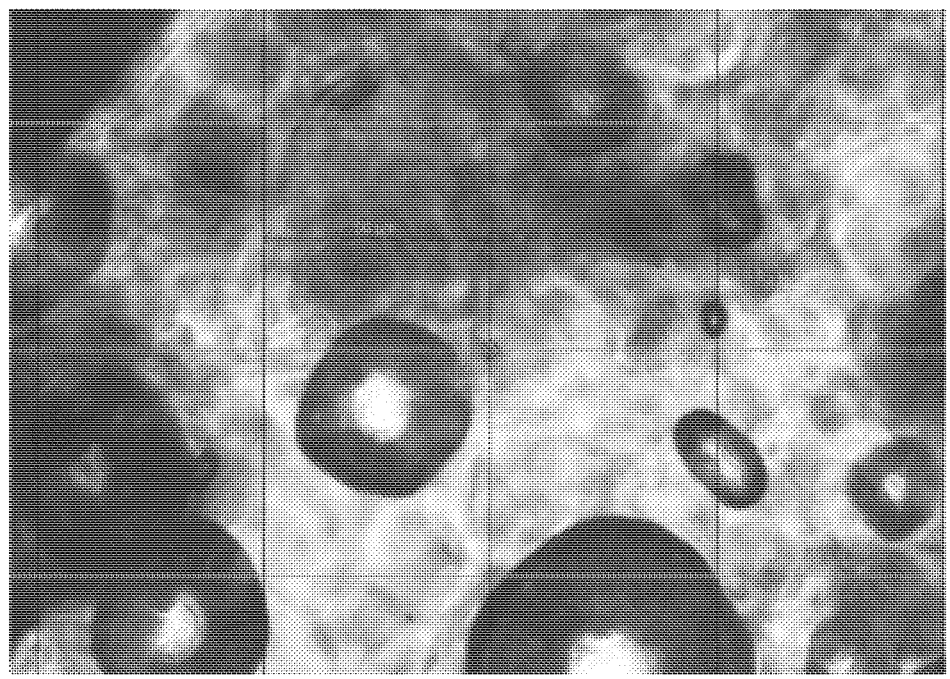

Referring to FIG. 8, in some embodiments, the pore size of the foam is between 1 to 500 microns in diameter. In some embodiments, the pore size of the foam is between 2 to 400 microns in diameter. In some embodiments, the pore size of the foam is between 2 to 300 microns in diameter. In some embodiments, the pore size of the foam is between 2 to 200 microns in diameter.

In some embodiments, the pore size of the foam is between 1 to 50 microns in diameter. In some embodiments, the pore size of the foam is between 2 to 10 microns in diameter.

In some embodiments, the pore size of the foam is between 10 to 500 microns in diameter. In some embodiments, the pore size of the foam is between 50 to 400 microns in diameter. In some embodiments, the pore size of the foam is between 100 to 400 microns in diameter. In some embodiments, the pore size of the foam is between 200 to 400 microns in diameter. In some embodiments, the pore size of the foam is between 300 to 400 microns in diameter.

In some embodiments, an anti-foaming agent, such as, for example, but not limited to, polydimethylsiloxane, polysorbate, etc, can be added to achieve a denser foam, where the denser foam can have a shear modulus of between 5 KPa to 15 KPa.

Without intending to be limited to any particular theory, in some embodiments, adding a biocompatible detergent and/or surfactant results in causing breaks to the foam, where the breaks are introduced before the foam stabilizes, and forms the reconstituted foam as a flowable gel. In some embodiments, the flowable gel can be mixed with a cross-linker solution (e.g., manually, mechanically or by pushing simultaneously through a static mixer) to generate a homogenous stabilized gel. In some embodiments, a confluent (i.e. as opposed to foam) stabilized gel can withstand degradation for an extended time in-vivo.

In some embodiments, the composition can include at least one surfactant. As used herein, "surfactant" refers to a compound that lowers the surface tension of water. In some embodiments, the surfactant may be an ionic surfactant, such as sodium lauryl sulfate, and octanoic acid; or a neutral surfactant, such as polyoxyethylene ethers, polyoxyethylene esters, and polyoxyethylene sorbitan.

In some embodiments, dextrin (dextran) can be added to the composition for decelerating in-vivo degradation kinetics.

In some non-limiting exemplary embodiments, in-growth of cells can be even further enhanced by adding a sulfated glycosaminoglycan (GAG), such as, for example, chondroitin sulfate. In some embodiments, the GAG can be added to a dry formulation of powders as co-polymer powder, chemically bonded to the protein/cross-linker (i.e., mTG), any other component before the jet-milling phase of preparation, or any combination thereof. In some embodiments, the concentration of GAG can be between 0.5% w/w to 10% w/w of the composition.

Without intending to be limited to any particular theory, cells within the porous scaffold may be involved in matrix interactions in three dimensions, similar to their experience within the fibrous environment of the natural extra cellular matrix. In comparison to 2D scaffolds or to scaffold materials that are less suitable, more naturalistic cell spreading, occurring in three dimensions, is achieved.

Without intending to be limited to any particular theory, the cells shape achieved in a three-dimensional porous scaffold may modify gene expression, protein translation and in turn function.

In some embodiments, cells are blended into the porous scaffold at preparation (mixed with the hydrating liquid) or enter the porous scaffold later, where they retain their natural 3D architecture. Thus, without intending to be limited to any particular theory, in some embodiments, the scaffold not only preserves the native 3D shape of individual cells, it also acts to bring cells together in a more natural manner. This results in the formation of tissue-like structures and cell-to-cell interactions that are more representative of normal tissue function.

In some embodiments utilizing gelatin, the cross-linked gelatin's elastic properties, as well as the abundance of integrin attachment sites (cell binding sites on the polymer) allow for cell ingrowth, proliferation and result in physiological tissue regeneration and enable various tissue engineering applications. In some embodiments, the cross-linked gelatin can create tissue-like structures in vitro with multiple cell types. Cells of different types can be brought together in 3D co-culture models, either as mixed populations or as discrete layers of different cell types. According to some embodiments the gelatin and cross-linker, such as mTG can be mixed with cell culture medium; containing, but not limited to the following substances: glucose, stable glutamine (Alanyl-Glutamine), Penicillin, $CaCl_2 \cdot 2H_2O$, Ferric Nitrate ($Fe(NO_3)_3 \cdot 9H_2O$), Potassium Chloride (KCl), $MgSO_4 \cdot 7H_2O$, Sodium Chloride (NaCl), Sodium Bicarbonate ($NaHCO_3$), Sodium Phosphate ($NaH_2PO_4$—$H_2O$), D-Glucose, Phenol Red, L-Alanyl-L-Glutamine, L-Arginine-Hcl, L-Cystine, Glycine, L-Histidine HCl—$H_2O$, L-Isoleucine, L-Leucine, L-Lysine-Hcl, L-Methionine, L-Phenylalanine, L-Serine, L-Threonine, L-Tryptophan, L-Tyrosine, L-Valine, D-Calcium pantothenate, Choline Chloride, Folic Acid, i-Inositol, Niacinamide, Pyridoxine Hcl, Riboflavin, Thiamine HCl and fetal bovine serum.

The mixing with the cell culture medium does not impair the cross-linking of the porous scaffold.

According to some embodiments, the gelatin and mTG dry powders can be mixed and hydrated with cell culture medium (containing, but not limited to the following substance: _Glucose, stable Glutamine (Alanyl-Glutamine), Penicillin, $CaCl_2 \cdot 2H_2O$, Ferric Nitrate ($Fe(NO_3)_3 \cdot 9H_2O$), Potassium Chloride (KCl), $MgSO_4 \cdot 7H_2O$, Sodium Chloride (NaCl), Sodium Bicarbonate ($NaHCO_3$), Sodium Phosphate ($NaH_2PO_4$—$H_2O$), D-Glucose, Phenol Red, L-Alanyl-L-Glutamine, L-Arginine-Hcl, L-Cystine, Glycine, L-Histidine HCl—$H_2O$, L-Isoleucine, L-Leucine, L-Lysine-Hcl, L-Methionine, L-Phenylalanine, L-Serine, L-Threonine, L-Tryptophan, L-Tyrosine, L-Valine, D-Calcium pantothenate, Choline Chloride, Folic Acid, i-Inositol, Niacinamide, Pyridoxine HCl, Riboflavin, Thiamine HCl and fetal bovine serum). In some embodiments, this allows for better survival of cells in initial gelatin-cells matrix. The cells may be mixed with the medium and held in one syringe while the mTG and gelatin powders are in another syringe. The syringes are then connected to each other with a locking mechanism allowing manual push to mix the ingredients together. By pushing them several times from one syringe to another, the cells, medium, gelatin, mTG and gas mix together to form an optimal scaffold seeded with cells. An exemplary embodiment showing viability of cells in a cross-linked gelatin porous scaffold of the present invention is detailed in Example 19.

In some embodiments, the inventive method can include modifying the perceived volume of the enzyme molecules in the cross-linked matrix being formed. In some embodiments, the modified perceived volume is determined according to the extent of crosslinking of the polymers to form the matrix, such that decreased extent of crosslinking, as compared with extent of crosslinking with unmodified enzyme molecules, indicates increased perceived volume. In some embodiments, one method of increasing the perceived volume of the enzyme molecules is by increasing the size and/or the hydrodynamic volume of the molecules by covalent or non-covalent attachment of at least one molecule or moiety to the enzyme molecules. In some embodiments, the method of the present invention includes use of a modified enzyme.

In some embodiments, a method of increasing the perceived volume is through modification of the electrostatic charge of the enzyme molecules such that their net charge is of opposite polarity to the net charge on the polymer or co-polymer chains. In an embodiment, increasing the perceived volume can be achieved by changing the isoelectric point (pi) of the enzyme.

According some embodiments of the composition of the present invention, there is provided a cross-linked porous scaffold, comprising a substrate polymer cross-linked by a modified enzyme molecule, where the modified enzyme molecule has a modification that alters a perceived volume of the enzyme molecules in the cross-linked matrix as the matrix is being formed through cross-linking of the polymer. In some embodiments, the modified enzyme molecule has a modification that increases an actual size of the modified enzyme molecule. In some embodiments, the modified enzyme molecule has a modification that increases a hydrodynamic volume of the modified enzyme molecule. In some embodiments, the modified enzyme molecule has a modification that modifies an electrostatic charge of the modified enzyme molecule to be of opposite sign to a net charge of the substrate polymer by changing the isoelectric point (pi) of the modified enzyme in comparison to unmodified enzyme. In some embodiments, the modification is of the ε-amino group of lysines of the enzyme through a process selected from the group consisting of succinylation (with succinic anhydride), acetylation (with acetic anhydride), carbamylation (with cyanate), reductive alkylation (aldehydes) and treatment with maleic anhydride. In some embodiments, the modification is of one or more side chains containing carboxylic acids of the enzyme to decrease the number of negative charges.

In some embodiments, the modification comprises covalent or non-covalent attachment of at least one molecule or moiety to the modified enzyme molecule. In some embodiments, the modification comprises covalent attachment of a modifying molecule to the modified enzyme molecule. In some embodiments, the modified enzyme molecule has a reduced diffusion rate and a reduced cross-linking rate in comparison to non-modified enzyme, but has at least similar measured enzyme activity in comparison to non-modified enzyme (e.g., but not limited to, about 20% to 100% activity compared with the non-modified enzyme).

In some embodiments, a reduced cross-linking rate is at least 10% of the non-modified enzyme cross-linking rate. In some embodiments, a reduced cross-linking rate is between 10%-40% of the non-modified enzyme cross-linking rate.

In some embodiments, the modifying molecule comprises a carrier or polymer. In some embodiments, the polymer comprises a synthetic polymer, a cellulosic polymer, a protein, a polysaccharide, or any combination thereof. In some embodiments, the cellulosic polymer comprises one or more of carboxymethyl cellulose, hydroxypropyl methylcellulose, hydroxyethyl cellulose, methyl cellulose, or any combination thereof. In some embodiments, the polysaccharide comprises one or more of dextran, chondroitin sulfate, dermatan sulfate, keratan sulfate, heparin, heparan sulfate, hyaluronic acid, a starch derivative, or any combination thereof.

In some embodiments of the composition of the present invention, the modifying molecule comprises PEG (polyethylene glycol). In some embodiments, PEG comprises a PEG derivative. In some embodiments, PEG derivative comprises activated PEG. In some embodiments, activated PEG comprises one or more of methoxy PEG (mPEG), its derivatives, mPEG-NHS, succinimidyl (NHS) esters of mPEG (mPEG-succinate-NHS), mPEG-glutarate, —NHS, mPEG-valerate-NHS, mPEG-carbonate-NHS, mPEG-carboxymethyl-NHS, mPEG-propionate-NHS, mPEG-carboxypentyl-NHS), mPEG-nitrophenylcarbonate, mPEG-propylaldehyde, mPEG-Tosylate, mPEG-carbonylimidazole, mPEG-isocyanate, mPEG-epoxide, or a combination thereof. In some embodiments, activated PEG reacts with amine groups or thiol groups on the enzyme. In some embodiments, the molar ratio of the activated PEG to lysine residues of the activated enzyme is in a range of from 0.5 to 25. In some embodiments, activated PEG is monofunctional, heterobifunctional, homobifunctional, or multifunctional. In some embodiments, activated PEG is branched PEGs or multi-arm PEGs. In some embodiments, activated PEG has a size ranging from 1000 Dalton to 40,000 Dalton.

In some embodiments, the porous scaffold further comprises a co-polymer that is not covalently bound to the enzyme or to the substrate polymer. In some embodiments, the co-polymer comprises a polysaccharide or a cellulosic polymer. In some embodiments, the polysaccharide comprises dextran, chondroitin sulfate, dermatan sulfate, keratan sulfate, heparin, heparan sulfate, hyaluronic acid, a starch derivative, or any combination thereof. In some embodiments, cellulosic polymer comprises carboxymethyl cellulose, hydroxypropyl methylcellulose, hydroxyethyl cellulose, methyl cellulose.

In some embodiments, a modified enzyme molecule is modified by cross-linking the modified enzyme molecule to a plurality of other enzyme molecules to form an aggregate of a plurality of cross-linked enzyme molecules. In some embodiments, a modification of the enzyme molecule affects at least one property of the matrix. In some embodiments, the at least one property is selected from the group consisting of tensile strength, stiffness, extent of crosslinking of the substrate polymer, viscosity, elasticity, flexibility, strain to break, stress to break, Poisson's ratio, swelling capacity and Young's modulus, or a combination thereof.

In some embodiments, an extent of modification of the modified enzyme determines mobility of the modified enzyme in, or diffusion from, the porous scaffold. In some embodiments, the modification of the modified enzyme reduces diffusion coefficient of the modified enzyme in a solution of the modified enzyme and the protein or in a porous scaffold of the modified enzyme and the protein, in comparison to a solution or porous scaffold of non-modified enzyme and the protein. In some embodiments, an extent of modification of the modified enzyme determines one or more foam mechanical properties. In some embodiments, the modified enzyme molecule shows a greater differential of crosslinking rate in crosslinked polymer than in solution as compared to non-modified enzyme molecule.

In some embodiments, the powdered cross-linker can be an enzyme and/or a modified enzyme to react with the powdered polymer. In some embodiments, the powdered polymer can be a protein, e.g., but not limited to, a gelatin.

In some embodiments, a gel-liquid transition point lowering agent is selected such as, by non-limiting example, urea or calcium. Such urea of calcium can be added to the dry formulation in dry powder forms. Such addition can increase the injectability of the mixed foam through thin needles. It will also collapse the foam in-situ to form a combination of porous scaffold and bulking confluent gel. The higher the concentration of such agents, the lesser scaffold and more confluent hydrogel will form. This can be suitable for some application but not others.

According to at least some embodiments of the present invention, there is provided a method for controlling formation of a matrix ("matrix" refers the hydrogel or porous scaffold), comprising modifying an enzyme molecule with a modification that alters a perceived volume of the enzyme molecules in the cross-linked matrix as the matrix is being formed; mixing the modified enzyme molecule with at least one substrate polymer that is a substrate of the modified enzyme molecule; and forming the matrix through cross-linking of the at least one substrate polymer by the modified enzyme molecule, wherein the forming the matrix is at least partially controlled by the modification of the enzyme molecule. In some embodiments, the modification reduces a crosslinking rate of the modified enzyme molecule as an extent of crosslinking of the at least one substrate polymer increases. In some embodiments, the modified enzyme molecule and the at least one substrate polymer are mixed in a micronized powder form, such that the modification controls extent of crosslinking of the at least one substrate polymer as a viscosity of the solution increases. In some embodiments, the modifying comprises PEGylation of the enzyme at a pH in a range from 7 to 9. In some embodiments, the pH of the PEGylation reaction is 7.5-8.5.

Guidance for calculation of formula gelatin dilution ("DG"):

For a formula containing both gelatin and mTG in maltodextrin carrier:

X gr gelatin+Y gr maltodextrin+Z gr liquid

Dilution of gelatin is equal to DG % w/w=100*X/(X+Y+Z)

For example: 1 gr gelatin+1 gr maltodextrin+4 gr liquid=⅙=16.6% w/w.

For a formula containing gelatin only:

X gr gelatin+Z gr liquid

Dilution of gelatin is equal to DG % w/w=100*X/(X+Z)

For example: 1 gr gelatin+4 gr liquid=⅕=20% w/w.

The above calculations assume the following:

1 gr gelatin=1 gr mTG in maltodextrin carrier=1 gr liquid;

1 ml of liquid=1 gr of liquid; and weight of enzyme is negligible in comparison to the other components.

Guidance for calculation of formula enzyme dilution ("DE"):

For a formula containing mTG in maltodextrin carrier:

X gr gelatin, Y gr maltodextrin, E gr enzyme, Z gr liquid

Dilution of Enzyme is equal to DE % w/w=100*E/(X+Y+E+Z)

The above calculation assumes that:

1 mg enzyme=10 units activity;

1 gr gelatin=1 gr maltodextrin=1 gr liquid; and 1 ml of liquid=1 gr of liquid.

For a formula containing mTG without maltodextrin:

X gr gelatin, E gr enzyme, Z gr liquid

Dilution of Enzyme is equal to DE % w/w=100*E/(X+E+Z)

The above calculation assumes that:

1 mg enzyme=10 units activity;

1 gr gelatin=1 gr liquid, the amount of enzyme is negligible; and 1 ml of liquid=1 gr of liquid.

Methods of Treating a Patient in Need Thereof

In one embodiment, the present invention provides a method, wherein the method stimulates fibroblasts to produce new collagen in a patient, comprising:
 a) forming a composition in the patient in an amount sufficient to induce fibroblasts stimulation,
 b) wherein the composition is configured to promote fibroblast stimulation and collagen synthesis, wherein the fibroblast attachment and collagen synthesis induce tissue (skin) rejuvenation, and
 c) wherein the composition is a porous scaffold,
 d) wherein the pores of the scaffold are from 1 to 500 microns, the composition comprising:
  i. a cross-linkable protein selected from the group consisting of collagen and gelatin;
  ii. a cross-linker which induces cross-linking of the cross-linkable protein; and
  iii. a liquid.

In one embodiment, the gelatin is present in the composition in the range of 3% w/w to 30% w/w after dilution with a liquid.

In one embodiment, the gelatin is present in the composition in the range of 8% w/w to 25% w/w after dilution with a liquid.

In one embodiment, the gelatin is present in the composition in the range of 9% w/w to 20% w/w after dilution with a liquid.

According to at least some embodiments, there is provided a composition for a vehicle for localized drug delivery, comprising a porous scaffold as described herein. According to at least some embodiments, there is provided a composition for tissue engineering, comprising a matrix as described herein, adapted as an injectable porous scaffold. According to at least some embodiments, a method of modifying a composition, includes: providing a modified enzyme having a cross-linkable functional group and a protein having at least one moiety cross-linkable by the modified enzyme; and mixing the modified enzyme and the protein, wherein the modified enzyme cross-links the protein and is also cross-linked to the protein through the cross-linkable functional group.

According to some embodiments, the composition is used as a vehicle for localized drug delivery. According to some embodiments, the composition is an injectable scaffold or tissue remodeling agent for tissue engineering and repair. According to at least some embodiments, there is provided a composition for a vehicle for localized delivery of lidocaine or other analgesic agents, comprising a porous scaffold as described herein.

As used herein, "bulking agents" are space-filling injectable substances used to increase tissue bulk. They can be injected under the skin for improved cosmetic results, periurethrally to treat urinary incontinence and perianally to treat fecal incontinence.

In some embodiments, the composition of the present invention is a bulking agent configured to be non-migrating, durable, degradable, is configured to be replaced by soft connective tissue over a prolonged period of time, or any combination thereof. In some embodiments, migration is a function of particles size and number. In some embodiments, the composition provides a scaffold for cells, endogenous or exogenous that proliferate and maintain the volumetric effect over time.

In some embodiments, the composition is an in-situ cross-linked gel so as to result in a stable and single consolidated physical formation. In some embodiments, the composition is degradable, and can be infiltrated by fibroblasts and immune cell gradually without risk of dislocation, and is configured to be replaced by tissue.

In some embodiments, the composition of the present invention is degraded by the body over time. In some embodiments, at least 70% to 100% of the composition is degraded after 3 months. In some embodiments, at least 70% to 100% of the composition is degraded after 6 months. In some embodiments, at least 75% to 100% of the composition is degraded after 3 months. In some embodiments, at least 75% to 100% of the composition is degraded after 6 months. In some embodiments, at least 80% to 100% of the composition is degraded after 3 months. In some embodiments, at least 80% to 100% of the composition is degraded after 6 months. In some embodiments, at least 90% to 100% of the composition is degraded after 3 months. In some embodiments, at least 90% to 100% of the composition is degraded after 6 months. In some embodiments, at least 70% of the composition is degraded after 3 months. In some embodiments, at least 75% of the composition is degraded after 3 months. In some embodiments, at least 80% of the composition is degraded after 3 months. In some embodiments, at least 85% of the composition is degraded after 3 months. In some embodiments, at least 90% of the composition is degraded after 3 months. In some embodiments, at least 95% of the composition is degraded after 3 months. In some embodiments, at least 100% of the composition is degraded after 3 months. In some embodiments, at least 70% of the composition is degraded after 4 months. In some embodiments, at least 75% of the composition is degraded after 4 months. In some embodiments, at least 80% of the composition is degraded after 4 months. In some embodiments, at least 85% of the composition is degraded after 4 months. In some embodiments, at least 90% of the composition is degraded after 4 months. In some embodiments, at least 95% of the composition is degraded after 4 months. In some embodiments, at least 100% of the composition is degraded after 4 months. In some embodiments, at least 70% of the composition is degraded after 5 months. In some embodiments, at least 75% of the composition is degraded after 5 months. In some embodiments, at least 80% of the composition is degraded after 5 months. In some embodiments, at least 85% of the composition is degraded after 5 months. In some embodiments, at least 90% of the composition is degraded after 5 months. In some embodiments, at least 95% of the composition is degraded after 5 months. In some embodiments, at least 100% of the composition is degraded after 5 months. In some embodiments, at least 70% of the composition is degraded after 6 months. In some embodiments, at least 75% of the composition is degraded after 6 months. In some embodiments, at least 80% of the composition is degraded after 6 months. In some embodiments, at least 85% of the composition is degraded after 6 months. In some embodiments, at least 90% of the composition is degraded after 6 months. In some embodiments, at least 95% of the composition is degraded after 6 months. In some embodiments, at least 100% of the composition is degraded after 6 months.

In some embodiments, the composition of the bulking agent can be an in-situ cross-linking porous scaffold, foam or a gel so as to result in a stable and single consolidated physical formation. In some embodiments, the composition is composed of dry micronized powders of gelatin and cross-linker. In some embodiments, the composition is composed of liquid state gelatin and cross-linker (in preferred embodiment the cross-linker is a transglutaminase). In some embodiments, the composition is composed of liquid state gelatin and cross-linker, where other excipients are used with the gelatin to reduce its natural solid-gel transition point (such as urea and calcium) to reduce its viscosity, and where the liquid transglutaminase contains excipients to enhance its stability and increase its viscosity.

In some embodiments the foamed gelatin can be delivered through a long and thin catheters or needles. In some embodiments, the method of the present invention is to deliver the gelatin in-situ stabilizing foam through a hollow delivery tube, which is at least 10 cm long and at most 10 French in diameter. In some embodiments, the method of the present invention is to deliver the gelatin in-situ stabilizing foam through a hollow delivery tube, which is at least 15 cm long and at most 6 French in diameter. In some embodiments, the method of the present invention is to deliver the gelatin in-situ stabilizing foam through a hollow delivery tube, which is at least 25 cm long and at most 6 French in diameter. In some embodiments, the method of the present invention is to deliver the gelatin in-situ stabilizing foam through a hollow delivery tube, which is at least 30 cm long and at most 6 French in diameter. In some embodiments the foamed gelatin can be delivered through a needle, which is at least 30-gauge in diameter. In some embodiments the foamed gelatin can be delivered through a, needle, which is at least 27-gauge in diameter. In some embodiments the foamed gelatin can be delivered through a needle, which is at least 25-gauge in diameter. In some embodiments the foamed gelatin can be delivered through a needle, which is at least 23-gauge in diameter. In some embodiments the foamed gelatin can be delivered through a needle, which is at least 21-gauge in diameter. In some embodiments the foamed gelatin can be delivered through a needle, which is at least 18-gauge in diameter.

In some embodiments, the bulking agent of the present invention is configured to remove or improve acne scars and correct wrinkle lines, elevate existing scars, resurface facial contours, or any combination thereof.

In some embodiments, the bulking agent of the present invention is a filling material having the following qualities: (i) Physiologic—Incorporates itself with the body's tissues; (ii) Simple procedure—Injectable; (iii) Risk-free—No complications or adverse effects; (iv) Semi Permanent—degrades with time; (v) serve as scaffold for ingrowth of cells and tissue remodeling agent or any combination thereof.

In some embodiments, the composition of the present invention is a filler, e.g., an intradermal filler. In some embodiments, the filler can be composed of gelatin and transglutaminase stabilizer. In some embodiments, the compositions of the present invention can be used to treat house pets, e.g., but not limited to, cats and dogs.

In some embodiments, the present invention is a method for stimulating fibroblasts to produce new collagen in a patient tissue, wherein an injectable tissue matrix bio-engineered specifically to function for fibroblasts focal adhesion is used. In some embodiments, the injectable tissue matrix is made of a biodegradable crosslinked protein (such as but not limited to gelatin) foam, it cross-links in-situ by microbial transglutaminase to form a stable and adhesive porous matrix with ideal mechanical properties. Such structure provides optimal mechanical and biological support to stimulate cell in-growth and allow a correct cross-talk between the matrix and fibroblasts. By mimicking the extra cellular matrix of the tissue natural environment, a de-novo cell rich tissue or dermal layer can be grown, having biological and structural properties of a young skin. The foam degrades and is eventually replaced by a native like architecture. The disclosed tissue matrix, provided in an embodiment of the present invention, will enable the growth and proliferation of fibroblasts, secretion of collagen and stimulated ECM buildup in the augmented site, as the foam described herein is slowly degraded by the body, thereby producing a biological tissue and/or skin rejuvenation.

In some embodiments of the present invention, the gelatin foam scaffold biomaterial can introduce integrin binding sites to the fibroblasts environment. Furthermore, through its favorable mechanical characteristics and its adhesiveness along with its abundance of RDGs (integrin attachment sites), it will exert bio-mechanical signals, previously lost to the endogenous ECM, into a treated site. Such bio-mechanical signaling by the said scaffold forms focal adhesion and stimulates fibroblasts collagen production while attenuating MMPs production. This allows the gelatin foam scaffold integration with the body. It can further transduce any biomechanical signals to its nearby environment causing a shift of phenotype in neighboring cells. Eventually, the gelatin foam scaffold biomaterial will degrade but not before the stimulated fibroblasts manufacture new interconnected collagen ECM to support their own and their neighboring cells, resulting in long lasting skin rejuvenation.

In some embodiments of the present invention, the gelatin foam scaffold biomaterial can induce collagen production from preexisting fibroblasts, induce their proliferation, and induce fibroblasts maturation from mesenchymal lineage cells and fibrocytes. It can further encourage cell infiltration into the foam volume, causing fibroblasts to produce ECM inside the foam volume. Such a process of foam degradation and ECM production will lead to a long-term effect in the augmented site. In other embodiments of the present invention, the gelatin foam scaffold material can also induce the formation of blood vessels to support the new cell population and matrix production. Those blood vessels will provide nutrient influx/efflux and promote the survival of such alterations, thereby making the effect long term. Thus, in some embodiments of the present invention, the gelatin foam scaffold biomaterial can support the rejuvenation of dermal skin suffering from natural or pathological conditions depending upon where more collagen production is needed.

In some embodiments of the present invention, the gelatin foam scaffold biomaterial can induce collagen production and will augment the collagen content of the sub-dermal supportive connective tissue such as, by non-limiting example, the septa, which enhances the appearance and texture of the skin.

In some embodiments of the present invention, the powders or gelatin foam scaffold biomaterial of the present invention are augmented with a peroxide to provide a solution for an open cell structure. In some embodiments of the present invention, there may be an advantage for an open cell (pore) foam over a closed cell foam. Thus, it is suggested that incorporating a soluble porogen mixed with the powders of the present invention will increase pore interconnectivity. While mixing a porogen powder with the other powders of the present invention, a porogen can be trapped inside the gelatin foam scaffold biomaterial. This porogen is activated by the contact of liquid and degrades into a gas form. The gas pressure builds up inside each closed cell to create cracks and links between adjacent pores. This provides for an oxygen-producing scaffold, which can alter the course of a given pathological condition and promote the reparative process including, but not limited to, cell proliferation and collagen synthesis.

In some embodiments of the present invention, the cross-linked gelatin foam scaffold biomaterial can be further deprived of liquids after full cross-linking. This can be done by desiccating, heat drying or freeze drying. The result foam is a stiff biomaterial that can be used for various applications. When the dry foam is hydrated, it returns to its flexible foam form, and can serve as a scaffold for cells in-vivo or in-vitro. Application of this dry form of the foam can be for example, but not limited to, drying the foam on implants, such as orthopedic implants, to enhance osteo-integration with the implant. Another application may be to use it for tissue augmentation and cellular activation. The dry foam can be particulated into small particles of 50-500 microns, such that it can be injected through a needle into a tissue such as, for example, dermal tissue.

In some embodiments of the present invention, the cross-linking enzyme will be purified to remove any manufacturing impurities and the resulting product will be less susceptible to immune response and degradation. As such, its in-vivo degradation profile can be slower and allows more time for neo-collagen build up (tissue remodeling). More collagen build up is translated into enhanced efficacy.

Reference is now made to the following examples, which together with the above descriptions illustrate some embodiments of the invention in a non-limiting fashion.

EXAMPLES

Example 1: Pull Tests on the Compositions, According to Some Embodiments of the Present Invention Components (i) 0.25 gr ACTIVA WM enzyme preparation (1% microbial transglutaminase from Streptoverticillium mobaraense, 99% maltodextrin) (Ajinomoto, Japan)

(ii) 0.25 gr Gelita 275 bloom, type A porcine gelatin (Gelita, Sioux City) medical grade low endotoxin, jet milled by Superfine Ltd to particle size of range: $d(0.1)=4.24$ um, $d(0.5)=16.61$ um, $d(0.9)=31.51$ um (iii) 1 ml saline (+ and liquid additive)

Method

Powders were sterilized by 9.93 KiloGray e-beam manufactured by L-3 Communications. Sterility was confirmed by AminoLab Ltd. (Rechovot, Israel), test was conducted according to SOP no. 50.WI.110-Sterility testing of health care products. Powders were mixed manually by pushing the mixture from one syringe to another for 10-12 times. Immediately thereafter the mixture was applied between two collagen sheets such that the glued overlap was approximately 2 cm*2.5 cm and left to cure for approximately 10 minutes. The composition was tested for maximum pull (sheer) force with a force gauge Lutron FG-20KG.

|  | test 1 [N] | test 2 [N] | test 3 [N] | test 4 [N] | test 5 [N] | Average results [N] | Average results [N/cm] |
|---|---|---|---|---|---|---|---|
| Non-sterile powders | 4.95 | 4.6 | 8.5 | 5.5* | 6.65* | 6.04 | 1.208 |
| Sterile powders | 6.75* | 6.6* | 3.25 | 4.2 | 7.1* | 5.58 | 1.116 |

Tearing observed not in the glue, but in failure of the collagen sheet itself, thus, the tear was not at the glued segment.

The results demonstrate the ability to terminally sterilize the micronized powders without significantly losing activity.

Example 2: Microscopy

The following Gelatin refers to Gelita 275 bloom, type A porcine gelatin (Gelita, Sioux City) medical grade low endotoxin, jet milled by Superfine Ltd to particle size of range: $d(0.1)=4.24$ um, $d(0.5)=16.61$ um, $d(0.9)=31.51$ um. The following mTG refers to ACTIVA (Ajinomoto, Japan).

Gelatin-mTG foam was prepared and visualized in a light microscope 10× and 40× magnifications to evaluate its foam properties.

Results:

Bubbles detected to be locked in a random fashion across the body element. The bubbles varied in size from 1 to 500 microns in diameter.

Example 3: Delivery of a Composition According to Some Embodiments of the Present Invention Via a Needle The following Gelatin refers to Gelita 275 bloom, type A porcine gelatin (Gelita, Sioux City) medical grade low endotoxin, jet milled by Superfine Ltd to particle size of range: $d(0.1)=4.24$ $d(0.5)=16.61$ μm, $d(0.9)=31.51$ μm. The following mTG refers to ACTIVA (Ajinomoto, Tokyo).

The Gelatin powder was mixed with mTG in 1:1 ratio. 0.75 gram of the mix was manually mixed into foam with 2.63 ml of water at 26° C. The foam was pushed through an 18-gauge needle (D=1.03 mm); 150 mm long.

Results:

The foam was successfully delivered from the syringe through the needle. The foam stabilized after about 3 minutes and remained stable in 50° C. water (meaning it is not thermoreversible).

Example 4: Testing of Various Compositions According to Some Embodiments of the Present Invention The following Gelatin refers to Gelita 275 bloom, type A porcine gelatin (Gelita, Sioux City) medical grade low endotoxin, jet milled by Superfine Ltd to particle size of range:

(A): $d(0.1)=4.24$ μm, $d(0.5)=16.61$ μm, $d(0.9)=31.51$ μm.

(B): $d(0.1)=4.415$ μm, $d(0.5)=13.064$ μm, $d(0.9)=29.621$ μm.

(C): $d(0.1)=13.451$ μm, (C): $d(0.5)=94.66$ μm, $d(0.9)=423.785$ μm.

The gelatin powders were mixed with mTG enzyme: ACTIVA (Ajinomoto, Tokyo) and hydrated by manual mixing (two syringes connected, one with powders, one with water). The result was a foam which was tested in its ability to adhere two sheets of collagen and tested for thermoreversibility by submerging the article in a bath of 50° C. water.

| Powder type | Gelatin amount [gr] | mTG bulk (ACTIVA) amount [gr] | Water amount [ml] | Water temp [° C.] | Stabilization time [min] | Adherence of collagen | Thermo-reversibility check |
|---|---|---|---|---|---|---|---|
| A | 0.25 | 0.25 | 1.5 | 19 | 6:00 | strong | Stable |
| B | 0.25 | 0.25 | 1.5 | 19 | 8:00 | weak | Reversible |
| B | 0.25 | 0.25 | 1.5 | 19 | 105:00 | strong | Stable |
| C | 0.25 | 0.25 | 1.5 | 19 | 6:00 | weak | Stable |
| A e-beam sterilized | 0.25 | 0.25 | 1.5 | 19 | 8:00 | strong | Stable |

Example 5: Characterization of Bonding and Mechanical Properties of Gelatin Foam Cross-Linked with Transglutaminase The following Gelatin refers to Gelita 275 bloom, type A porcine gelatin (Gelita, Sioux City) medical grade low endotoxin, jet milled by Superfine Ltd to particle size of range: d(0.1)=4.24 μm, d(0.5)=16.61 μm, d(0.9)=31.51 μm. The following mTG refers to ACTIVA powder with a activity level of 100 U/gm (Ajinomoto, Tokyo). The mTG contains 1% enzyme and 99% maltodextrin. If specified Sterilized powders—Gelatin and mTG micronized powders were sterilized using gamma radiation 9.38 KGray (Sorvan, Israel)

The rheological parameters of the cross-linked foam were measured using The Lloyd Materials Testing LS1 machine (Ametek Test & Calibration Instruments), a 1 kN high precision material testing machine, was used to test the mechanical properties of the biological material. The biological material was prepared by manual mix per ratios specified in Table below and allowed 40 minutes between mixing and testing. It and injected onto a Teflon-covered glass plate, in between spacers and a glass cover with a Teflon surface, creating a 3 mm thick rectangular shape once stabilized. A standard dog-bone formation was punched from the biological material and used for mechanical testing. A tension test was performed by moving the upper grip upwards, stretching the biological material until failure (full tear). The maximum load and percent of total elongation at maximum force were determined based on the sample width and thickness. The Young's Modulus was calculated by choosing two points, which represent the most linear part of the graph. The test speed was 45 mm/minute and a 10 N load cell (Serial No. 10N0360) was used.

The burst pressure test was conducted based on ASTM F2392-04, The Standard Test Method for Burst Strength of Surgical Sealants. For each burst pressure test, collagen sausage casing (Nitta Casings, N.J.) was used as a substrate. A 3-mm diameter hole was punched in each casing specimen and each specimen was clamped into the specimen holding manifold. The foam was prepared by manual mixing the components, allowing a 40 minutes curing time. Then, the tissue manifold was filled with double distilled water and pressurized by syringe pump (KD Scientific Model 100 Series) activated at a rate of 120 mL/hour. Water filled the test fixture through silicone tubes and a pressure gauge was used to determine the maximum pressure (PSI) until failure. The type of failure (cohesive, adhesive) was recorded after each test. Three repeats were tested for each group.

Results:

The results depicted in the tables below, clearly demonstrate the ability to fabricate a biological material according to the present invention with mechanical properties that are easy to control to fit different needs in the field of tissue engineering or surgical sealing.

Lloyd Mechanical Testing:

| Formula used for calculations* | Average Max Load (N) | RSD (%) | % total elongation at max force | RSD (%) | Average Young's modulus (KPa) | RSD (%) | Notes: |
|---|---|---|---|---|---|---|---|
| 8 mL PBS + 1 g Gelatin + 1 g mTG | 0.2321 | 2.29 | 96.71 | 16.14 | 6.39 | 17.01 | |
| 4 mL PBS + 1 g Gelatin + 0.4 g mTG | 0.9378 | 23.93 | 134.62 | 16.92 | 5.90 | 20.64 | |
| 8 mL PBS + 1 g Gelatin + 0.4 g mTG | #N/A | #N/A | #N/A | #N/A | #N/A | #N/A | did not cross-link |
| 5 mL PBS + 1 g Gelatin + 1 g mTG | 0.5092 | 15.84 | 110.21 | 17.30 | 4.11 | 13.13 | |
| 5 mL PBS + 1 g Gelatin + 0.4 g mTG | 0.7031 | 21.81 | 189.51 | 19.54 | 4.27 | 13.13 | |

| Sample Group | % total elongation range at max force | Young's modulus range (KPa) | Formula used for calculations* |
|---|---|---|---|
| 8X (Group A) | 107.97 | 6.6534 | 8 mL PBS + 1 g Gelatin + 1 g mTG |
| | 78.896 | 5.1945 | |
| | 103.27 | 7.3197 | |

-continued

| Sample Group | % total elongation range at max force | Young's modulus range (KPa) | Formula used for calculations* |
|---|---|---|---|
| 4X (Group B) | 140.09 | 5.7127 | 4 mL PBS + 1 g |
|  | 109.6 | 4.7911 | Gelatin + 0.4 g mTG |
|  | 154.17 | 7.2052 |  |
| 5X (Group A) | 113.12 | 3.5044 | 5 mL PBS + 1 g |
|  | 89.859 | 4.5356 | Gelatin + 1 g mTG |
|  | 127.65 | 4.2965 |  |
| 5X (Group B) | 246.57 | 4.1400 | 5 mL PBS + 1 g |
|  | 173.14 | 4.7517 | Gelatin + 0.4 g mTG |
|  | 203.04 | 4.7785 |  |
|  | 150.03 | 4.2902 |  |
|  | 174.76 | 3.403 |  |

Burst Pressure Testing:

| Formula used for calculations* | Average Maximum PSI Burst pressure | RSD (%) |
|---|---|---|
| 6 mL PBS + 1 g Gelatin + 1 g mTG | 2.9000 | 5.97 |
| 8 mL PBS + 1 g Gelatin + 1 g mTG | 2.7667 | 13.68 |
| 4 mL PBS + 1 g Gelatin + 0.4 g mTG | 3.1667 | 11.96 |
| 8 mL PBS + 1 g Gelatin + 0.4 g mTG | 1.8667 | 21.65 |
| 4 mL PBS + 1 g Gelatin + 1 g mTG | 3.1333 | 12.90 |
| 2 mL PBS + 0.5 g Gelatin + 0.5 g mTG Sterilized powders | 1.2000 | 23.57 |
| 2 mL PBS + 0.4 g Gelatin + 0.4 g mTG Sterilized powders | 1.8667 | 22.30 |
| 2 mL PBS + 0.4 g Gelatin + 0.4 g mTG | 3.0000 | 5.77 |

Example 6: Characterization of Nutrient Penetration of a Crosslinked Gelatin Foam This example demonstrates the ability of a composition according to the present invention to allow nutrient circulation. Foams of the following composition were made by manual mixing the dry components by a method of passing PBS from one syringe containing the transglutaminase/gelatin composition to the other connected syringe 10 times and allowed to crosslink for 15 minutes before adding the colored media. 4 mL PBS+1 gr Gelatin and 1 gr mTG were mixed. The biological material had a diameter of 21 mm and thickness of 26 mm. Red Maimon's food coloring liquid dye was diluted in water, and the biological material was submerged in the colored liquid for 24 hours before cut in half to measure the color diffusion.

Example 7: Cell Survival after Mixing with Gelatin Component

The following Gelatin refers to Gelita 275 bloom, type A porcine gelatin (Gelita, Sioux City) medical grade low endotoxin, jet milled by Superfine Ltd to particle size of range: d(0.1)=4.24 μm, d(0.5)=16.61 μm, d(0.9)=31.51 μm. Gelatin micronized powders were sterilized using gamma radiation 9.38 KGray (Sorvan, Israel).

The following example aims to demonstrate the ability of Normal Human Dermal Fibroblasts (NHDF) to withstand the shear forces exhibited by the mixing needed to produce the composition according to the present invention and to assess the best method of cell incorporation inside the biological material, by direct mixing or by using a 3-way stopcock. As this method of mixing when used as a cell scaffold for tissue engineering purposes, ensures the homogenous spreading and viability of cells inside the scaffold volume.

NHDF cells were separated from 100 mm plates upon reaching a confluence of 80% using trypsin (Trypsin EDTA solution B (0.25%), EDTA (0.05%), with Phenol Red, Biological industries, 03-052-1A) treatment of 2 ml for 3-5 minutes following with counteracting the trypsin with 6 mL of serum containing media (Dulbecco's modified eagle's medium, High glucose, Biological industries Lot 1530279, supplemented with 10% Certified Foetal Bovine serum, Catalog #: 04-001-1A, and 1% Penicillin-Streptomycin solution, Biological Industries, 03-031-1C). Cells were centrifuged for 5 min at 1500 RPM and resuspended in 6 ml pre-heated media to give a stock concentration of 360,000 NHDFcells/ml.

Three repeats of mixing a gelatin powder with media containing cells as described in the table below were performed and cell survivability was demonstrated using trypan blue (0.5%) diluted 1:1 with cell containing media, and visual inspection 4, 24 hours post seeding. In well 1 the gelatin and media containing cells were mixed directly using 2 syringe system (male luer lock connected with female luer lock). While at wells 2-3 the gelatin was first solubilized using 2.5 ml media mixed for 8 times and immediately after, added with additional 1.5 ml media containing cells using a 3 way stop cock (Elcam Medical) and 2 additional mixing were done. Cells containing gelatin mix were seeded on top 6 well plate of tissue culture treated plastic (Corning Inc., Costar, Product #: 3516).

Adherence of cells was easily spotted 4 hours post seeding while at 24 hours post seeding the cells look fully spread on the plate which proves the cells are viable and able to withstand the shear stresses they are subjected to during the mixing.

Cell Survivability Assay Due to Shear Stress

| Well | Preparation | After 4 hours | After 24 hours |
|---|---|---|---|
| 1 | 0.5 g gelatin + 2.5 ml stock mixed in 2 syringe system | Confluent, adherent cells | Cells are well spread on the plastic |
| 2 | 0.6 g gelatin + 2.5 mL medium + 1.5 mL stock mixed with stopcock | Confluent, adherent cells | Cells are well spread on the plastic |
| 3 | 0.6 g gelatin + 2.5 mL medium + 1.5 mL stock mixed with stopcock | Confluent, adherent cells | Cells are well spread on the plastic |

Example 8: Cell Viability Inside a Cross-Linked Gelatin Foam

The following Gelatin refers to Gelita 275 bloom, type A porcine gelatin (Gelita, Sioux City) medical grade low endotoxin, jet milled by Superfine Ltd to particle size of range: d(0.1)=4.24 μm, d(0.5)=16.61 μm, d(0.9)=31.51 μm. The following mTG refers to ACTIVA WM, powder with an activity level of 100 U/gm (Ajinomoto, Tokyo). The mTG contains 1% enzyme and 99% maltodextrin. Gelatin and mTG micronized powders were sterilized using gamma radiation 9.38 KGray (Sorvan, Israel). Following Media refers to Serum containing media (Dulbecco's modified eagle's medium, High glucose, Biological industries (Israel), supplemented with 10% Certified Foetal Bovine serum, Catalog #: 04-001-1A, and 1% Penicillin-Streptomycin solution, Biological Industries, 03-031-1C).

The following example aims to demonstrate fibroblasts cells are able to survive and thrive being embedded or seeded in a composition according to this present invention, for 7 days or more.

The NHDF cells were separated from 100 mm plates upon reaching a confluence of 80% using trypsin (Trypsin EDTA solution B, Biological industries, 03-052-1A) treatment of 2 ml for 3-5 minutes following with counteracting the trypsin with serum containing media. Cells were centrifuged for 5 min at 1500 RPM and resuspended in media to give a stock concentration of 1,000,000 cells/ml.

Group A: A gelatin biological material with a composition of 200 mg sterilized gelatin mixed with 120 mg sterilized mTG, loaded on a male luer lock syringe and mixed with 1 ml of cell stock media (Dulbecco's modified eagle medium, high glucose, Biological industries Lot 1530279) for 10 times to fabricate the biological material, and injected onto 6 well plates of non-treated plastic (Corning Inc., Costar, Reference #: 3736, Lot #: 30015036).

Group B: Biological material of the same composition was mixed with media with no cells, allowed to cross link for 40 min, and 1×10^6 cells were added in a 3 ml media (Dulbecco's modified eagle's medium, high glucose, Biological industries Lot 1530279, supplemented with 10% Certified Foetal Bovine serum, Catalog #: 04-001-1A, and 1% Penicillin-Streptomycin solution, Biological Industries, 03-031-1C) put on a shaker for 2 hours at 37° C. before moved into an incubator with 5% CO2 and 37° C. O/N. This method allows the cells to attach onto the gelatin scaffold and grow on its periphery rather than be embedded within its volume.

Group C: Used as a control and contained no cells, but had the same composition of the biological material in Groups A and B, respectively.

Groups A, B, and C were incubated in an incubator with 5% CO2 and 37 degrees Celsius.

Twenty-four hours post-seeding, all groups were cut into quarters using a scalpel. Group B biological material was transferred to a new plastic 6 well plates not treated for cell culture to separate tested article from the cells that were not attached to the biological material, and then 10% Alamarblue v/v was added to all wells. The Alamarblue reduction was measured 3 days and 6 days post cell seeding. Proximally 24 hours allowed for the Alamarblue reaction.

Figure 10:
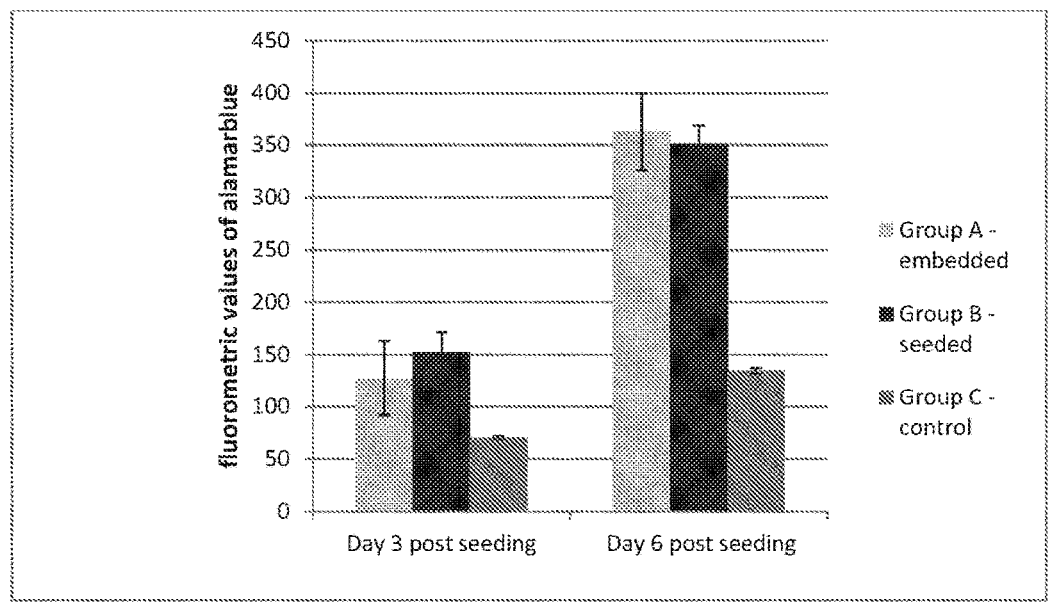
FIG. 10 shows the viability of cells seeded in a scaffold composition according to some embodiments of the present invention.

Results:

The results depicted in FIG. 10, clearly demonstrate that the cells either inside the biological material (Group A) and on the biological material (Group B) are viable and able to reduce the Alamarblue at the designated time points shown by the different coloring of the Alamarblue containing media compared to the control (Group C). Those results support the claim that the crosslinked gelatin foam biological material can act as a good scaffold for tissue engineering purposes.

Example 9: Subcutaneous Injections of a Composition According to Some Embodiments of the Present Invention The following Gelatin refers to Gelita 275 bloom, type A porcine gelatin (Gelita, Sioux City) medical grade low endotoxin, jet milled by Superfine Ltd to particle size of range: d(0.1)=4.24 μm, d(0.5)=16.61 μm, d(0.9)=31.51 μm. The following mTG refers to ACTIVA WM, powder with an activity level of 100 U/gm (Ajinomoto, Tokyo). The mTG contains 1% enzyme and 99% maltodextrin. Gelatin and mTG micronized powders were sterilized by 9.93 KiloGray e-beam (Sorvan, Israel). The tested composition comprised: 0.25 gr gelatin powder+0.25 mTG powder in one syringe was mixed with 1 ml of sterile saline.

Two 60 kg SW swine were used for the study. Animals were anesthetized and an injection of the tested composition (0.3-0.5 ml foam) was performed under the skin using a needle in left front leg. After 90 days follow up period the animals were euthanized and tissue harvested for microscopic analysis. The tissue samples were fixated in formalin and sent for preparation of slide and hematoxylin and eosin staining.

Results:

None of the animals have shown any adverse effects. The biomaterial presents good tolerability and was mostly degraded. Neither necrosis nor cavity formation nor migrations were noted.

FIG. 2A illustrates fibroblasts in location treated tissue at 90-days post-injection. As illustrated in FIG. 2A, the fibroblasts were plump, spindle shaped or stellate shaped cells with centrally placed oval or round nuclei. This was shown by their basophilic staining. Together these findings suggest that those fibroblasts were activated and were able to produce new collagen.

FIG. 2B illustrates fibroblasts in non-treated tissue at 90-days post-injection. As illustrated in FIG. 2B, the fibroblasts were thin and flat with wavy nuclei and their cytoplasmic volume was reduced suggesting non-active fibroblasts in a mature phase.

The composition of the present invention can stimulate fibroblasts activation and new collagen production suggesting it can help in rebuilding or restoring damaged ECM. In the case of skin application, this is expected to make the skin look and feel like younger skin.

Example 10: Cell Morphology on Scaffold Using Scanning Electron Microscope for Imaging The following gelatin refers to Gelita 275 bloom, type A porcine gelatin (Gelita, Sioux City) medical grade low endotoxin, jet milled by Superfine Ltd to particle size of range: d(0.1)=4.24 μm, d(0.5)=16.61 μm, d(0.9)=31.51 μm. The following mTG refers to ACTIVA WM, powder with an activity level of 100 U/gm (Ajinomoto, Tokyo). The mTG contains 1% enzyme and 99% maltodextrin. Gelatin and mTG micronized powders were sterilized using gamma radiation 9.38 KGray (Sorvan, Israel). Gelatin: mTG ratio was 1 U mTG/10 mg gelatin. Following Media refers to Serum containing media (Dulbecco's Modified Eagle's medium, High glucose, Biological industries (Israel), supplemented with 10% Certified Foetal Bovine serum, Catalog #: 04-001-1A, and 1% Penicillin-Streptomycin solution, Biological Industries, 03-031-1C).

The NHDF cells were separated from 100 mm plates upon reaching a confluence of 80% using trypsin (Trypsin EDTA solution B, Biological industries, 03-052-1A) treatment of 2 ml for 3-5 minutes following with counteracting the trypsin with serum containing media. Cells were centrifuged for 5 min at 1500 RPM and resuspended in media to give a stock concentration of 1,000,000 cells/ml.

Micronized Gelatin and mTG powders mixed in one syringe were mixed with Media with no cells, allowed to cross link for 40 min, and 1×10^6 cells were added in a 3 ml media (Dulbecco's modified eagle's medium, high glucose, Biological industries Lot 1530279, supplemented with 10% Certified Foetal Bovine serum, Catalog #: 04-001-1A, and 1% Penicillin-Streptomycin solution, Biological Industries, 03-031-1C) put on a shaker for 2 hours at 37° C. before moved into an incubator with 5% CO2 and 37° C. O/N. This method allows the cells to attach onto the gelatin scaffold and grow on its periphery rather than be embedded within its volume.

Following 7 days incubation, parts of the scaffold were gently cut. The scaffold with the cells was fixated using 4% paraformaldehyde for 24 hours at 4° C. The scaffold was then dehydrated in a graded acetone series (30, 50, 70, 80, 90, 95, 100). Followed by drying with a balzers CPD 030 Critical Point Dryer (CPD). Samples were coated with gold sputter before SEM examination.

Figure 4:
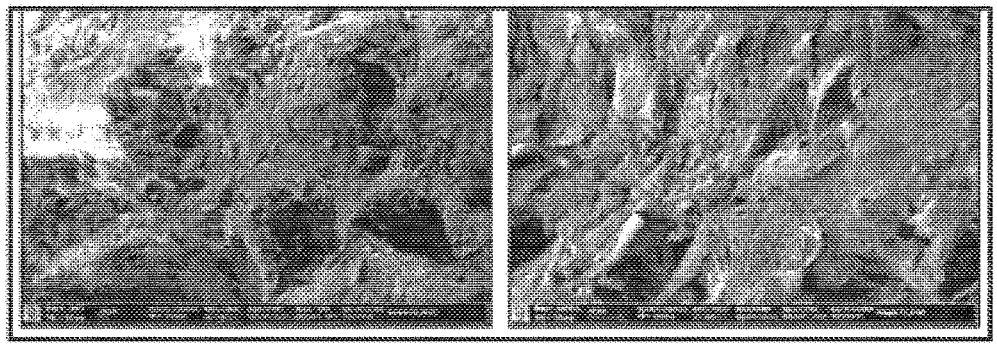
FIG. 4 are photographs showing cells seeded in a scaffold composition according to some embodiments of the present invention.

FIG. 4 illustrates cells seeded in a scaffold composition according to some embodiments of the present invention.

Results:

The fibroblasts were found to populate the scaffold surface and its pores. Seeded fibroblasts visualized in a spindle shaped morphology rather than flat or rounded as maybe expected from them in-vitro. This morphology can also be described as elongated, representing the phenotype of young fibroblasts. The cells are also able to form bonds between themselves. Such results demonstrate that the crosslinked gelatin foam can affect fibroblasts phenotype promoting new collagen production and tissue rejuvenation.

Example 11: Comparison of the Ability for Collagen Deposition of Different Dermal Fillers Versus a mTG Crosslinked Gelatin Foam In Vivo The following Gelatin refers to Gelita 275 bloom, type A porcine gelatin (Gelita, Sioux City) medical grade low endotoxin, jet milled by Superfine Ltd to particle size of range: $d(0.1)=4.24$ μm, $d(0.5)=16.61$ μm, $d(0.9)=31.51$ μm. The following mTG refers to ACTIVA WM, powder with an activity level of 100 U/gm (Ajinomoto, Tokyo). The mTG contains 1% enzyme and 99% maltodextrin. Gelatin and mTG micronized powders were sterilized using gamma radiation 9.38 KGray (Sorvan, Israel). Gelatin: mTG ratio was 1 U mTG/10 mg gelatin.

One 90 kg Large White crossed with Red Duroc swine, 10-month old, was used for the study. The animal was anesthetized and an injection of the tested composition (1.6-2.4 ml foam) or a commercially available dermal filler were injected as follows: 6 skin areas of at least 5×5 cm were chosen on the ventral area of the pig. A cannula was inserted medially to a medial point of each area to evenly distribute different skin enhancing dermal fillers and the tested composition of mTG crosslinked gelatin foam.

The dermal fillers injected:

Commercial dermal fillers were used as instructed by the manufacturer (Restylane Vital, SCULPTRA, Radiesse, Restylane).

| | A | B | C | D | H | F |
|---|---|---|---|---|---|---|
| Dermal fillers | Saline control | Restylane Vital (Hyaluronic acid) "Skin Booster" | SCULPTRA (PLLA) | Radiesse (Calcium Hydroxylapatite) | Restylane (Hyaluronic acid) | 400 mg gelatin + 400 mg Activa-WM + 2.4 ml Saline |

Sample collection: 7 mm punch biopsies were taken at 30 days, 60 days, 90 days, and 150 days post-injection, submerged in 10× volume 4% paraformaldehyde and further embedded in paraffin. Blocks were sectioned to 5 μm slices and stained for hematoxylin and eosin for cell infiltration and tissue response analysis and Masson's trichrome stain for collagen deposition analysis Results:

A grading histopathological analysis of different dermal fillers versus mTG crosslinked gelatin foam (Group F) at 12 and 30 days post injection.

| Filler injected and the number of days following injection | Control (Saline) | | Restylane Vital | | Sculptra | | Radiesse | | Restylane | | Group F | |
|---|---|---|---|---|---|---|---|---|---|---|---|---|
| | 12 | 30 | 12 | 30 | 12 | 30 | 12 | 30 | 12 | 30 | 12 | 30 |
| Remnants of implanted material | 0 | 0 | 2 | 2 | 1 | 1 | 2 | 2 | 2 | 2 | 1 | 1 |
| New collagen fibers | 0 | 0 | 1 | 0-1 | 1 | 1 | 1-2 | 1 | 1-2 | 1 | 2-3 | 2-3 |
| Inflammatory response (macrophages., giant cells, lymphocytes) | 1* | 0 | 2 | 2 | 1 | 2 | 2** | 0-1 | 1 | 2 | 1** | 2 |
| Foreign body response | 0 | 0 | 2 | 2 | 1 | 2 | 2 | 1 | 2 | 2 | 2 | 1 |

Using a semi-quantitative grading of five grades (0, 1, 2, 3, 4), taking into consideration the severity of the changes (0=No Lesion, 1=Minimal change, 2=Mild change, 3=Moderate change, 4=Marked change). *—lesion was formed due to needle trauma, **—high presence of lymphocytes were seen.

All materials were shown to cause foreign body granulation response. Cell infiltrate was mostly composed of macrophage and giant cells and the materials had a degradation pattern characterized of absorption by giant cells engulfing the foreign material. No adverse effects such as necrosis, edema, or calcification were shown in any of the materials tested.

Figure 5:
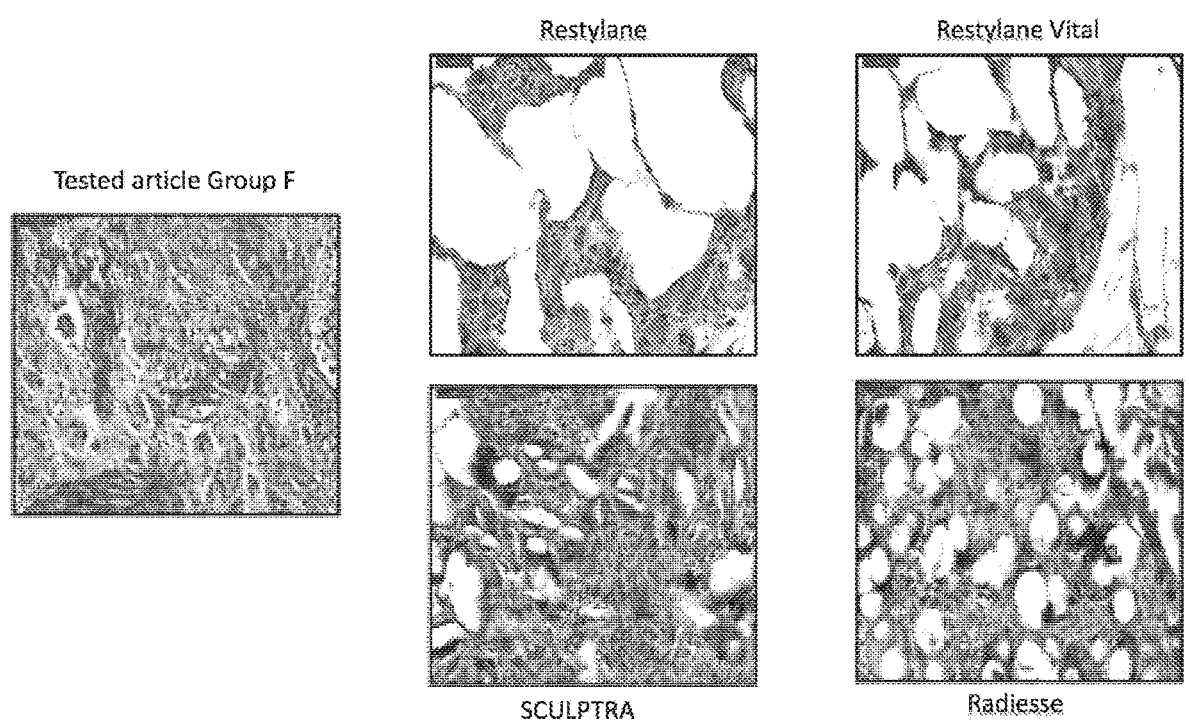
FIG. 5 are photographs of collagen deposition analysis, according to some embodiments of the present invention.
Figure 6A:
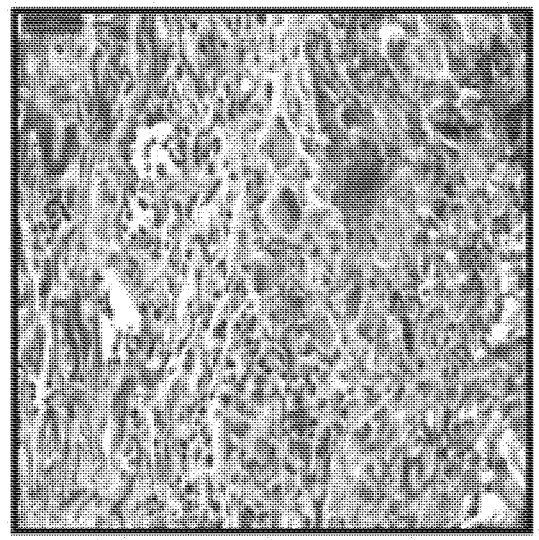
FIGS. 6A-6E are photographs of compositions of the present invention according to some embodiments of the present invention.
Figure 6B:
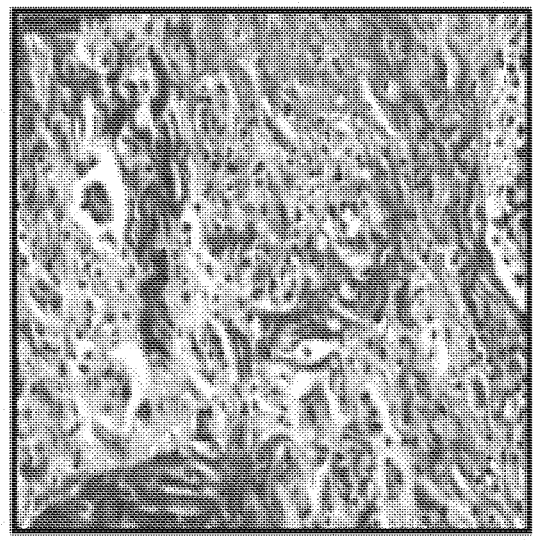
Figure 6C:
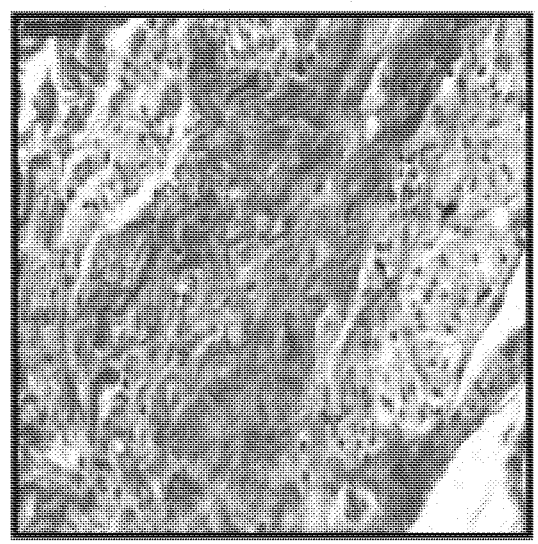
Figure 6D:
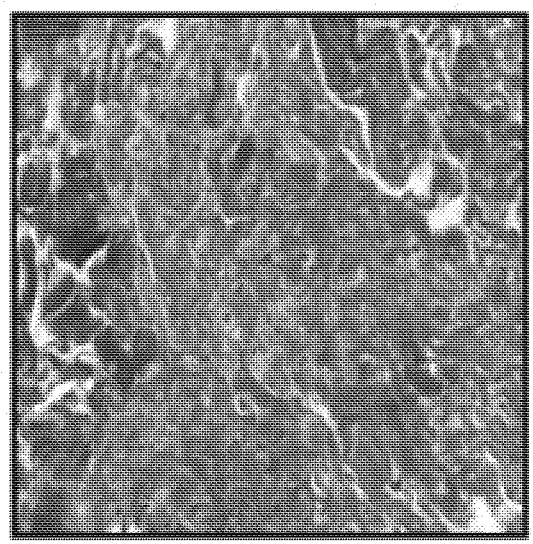
Figure 6E:
Figure 7A:
FIGS. 7A-D are photographs of compositions of the present invention according to some embodiments of the present invention.
Figure 7B:
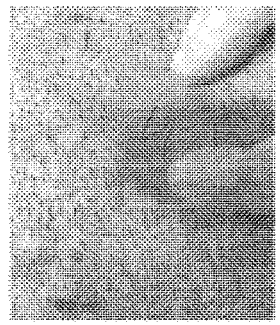
Figure 7C:
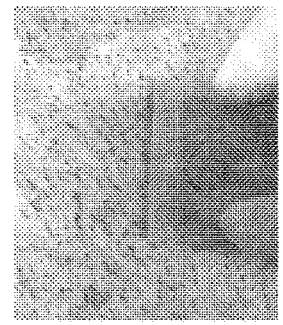
Figure 7D:
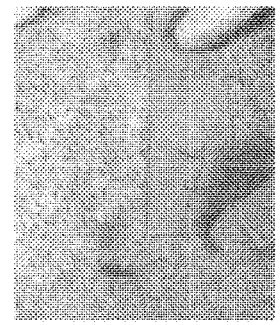

FIG. 5 illustrates the collagen deposition of different dermal fillers compared to Group F at 30 days post injection.

Masson's trichrome staining of different dermal fillers and the mTG crosslinked gelatin foam scaffold biomaterial clearly show collagen deposition stain in blue. Collagen deposition in the mTG crosslinked gelatin foam is superior in quantity and organization. The collagen fibers appear to be organized in parallel whereas, in commercially available dermal fillers, the collagen fibers are disorganized.

FIGS. 6A-6E illustrate compositions of the present invention according to embodiments of the present invention.

The images are histopathological sections colored by Masson's trichrome staining of subdermal tissue treated with the said crosslinked gelatin foam scaffold biomaterial. The images are from 12 days, 30 days, 60 days, 90, 150 days post injection. Demonstrating the development of new organized collagen fibers at the treated site. Mainly the septa of the sub-dermis are augmented with thicker collagen content. The new collagen is stained blue.

Conclusions

At 12-day histological examination, abundant fibroblasts were already present in the implantation site of Group F (crosslinked gelatin foam scaffold biomaterial). This phenomenon was not observed in the other known fillers.

Twelve days following the injection of Group F, histological examination demonstrated a mild grade inflammatory response, which was equivalent to other commercial materials. To note, minimally higher presence of giant cells, macrophages and lymphocytes were present compared to already highly-purified commercial products (this can be explained by the impurity of the tested product, which is not yet clinical grade).

Thirty days following the injection of Group F, many collagen fibers were observed in the implantation site. The amount of new collagen deposits following Group F injection was significantly higher (score 2-3) compared to the other tested material (score 0-1). Following Group F injection, no necrosis, cavity formation or edema were present, demonstrating good tissue tolerability.

One hundred and fifty days following the injection of Group F, it is noticed that the fibrotic septea at the hypodermis is augmented and thickened. The fibers look organized wavy and natural rather than disorganized as in scarred or fibrotic tissue, indicating that collagen type I is produced following the injection of the crosslinked gelatin. No necrosis, cavity formation or edema were present.

Example 12: Increasing the Injectability of a Viscous Material

The following gelatin refers to Gelita 275 bloom, type A porcine gelatin (Gelita, Sioux City) medical grade low endotoxin, jet milled by Superfine Ltd to particle size of range: d(0.1)=4.24 μm, d(0.5)=16.61 μm, d(0.9)=31.51 μm. The following mTG refers to ACTIVA WM, powder with an activity level of 100 U/gm (Ajinomoto, Tokyo). The mTG contains 1% enzyme and 99% maltodextrin. Gelatin and mTG micronized powders were sterilized using gamma radiation 9.38 KGray (Sorvan, Israel). Gelatin: mTG ratio was 1 U mTG/10 mg gelatin.

Results:

Micronized gelatin powder was screened (cut off larger particles) to reduce the size of gelatin particles and narrow the particle distribution range. It was detected that when screening the gelatin powder with a net containing a pore size of a specific range, the foam initial viscosity can be adjusted after mixing and thus can be injected through needles of varying gauges. This allows modification of the foam injectability, which allows a physician to easily treat fine wrinkles without damaging a patient's skin.

The table below describes the improvements in the injectability.

| Screen average pore size (μm) | Maximum needle gauge for easy injection |
|---|---|
| 20 | 28 |
| 50 | 25 |
| 100 | 22 |

Example 13: Adjusting the Scaffold's In-Vivo Functionality

The following gelatin refers to Gelita 275 bloom, type A porcine gelatin (Gelita, Sioux City) medical grade low endotoxin, jet milled by Superfine Ltd to particle size of range: d(0.1)=4.24 μm, d(0.5)=16.61 μm, d(0.9)=31.51 μm. The following mTG refers to ACTIVA WM, powder with an activity level of 100 U/gm (Ajinomoto, Tokyo). The mTG contains 1% enzyme and 99% maltodextrin. Gelatin and mTG micronized powders were sterilized using gamma radiation 9.38 KGray (Sorvan, Israel). Gelatin: mTG ratio was 1 U mTG/10 mg gelatin.

One 90 kg Large White crossed with Red Duroc swine, 10-months old, was used for the study. The animal was anesthetized and an injection of the tested compositions, various gelatin to liquid dilutions, were tested and evaluated for collagen production at 30 days post injection.

Results:

It was detected that by adjusting the ratios of the components (i.e., liquid, gelatin, mTG) the amount of collagen production can be optimized. The table below describes the amount of collagen produced as dependent on the ratio between gelatin and liquid (mTG enzyme remains constant). Gelatin % w/w of 12.5-8% w/w are likely more effective than higher tested concentrations of gelatin such as the 16.6% w/w.

| Gelatin w/w % after dilution | Collagen production; % of maximum effect |
|---|---|
| 16.6 | 70 |
| 12.5 | 100 |
| 8 | 100 |

Figure 11A:
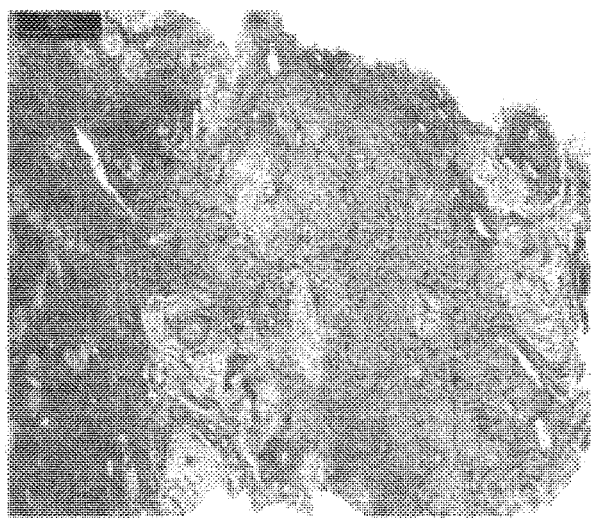
FIGS. 11A and 11B are photographs of compositions of the present invention according to some embodiments of the present invention.
Figure 11B:
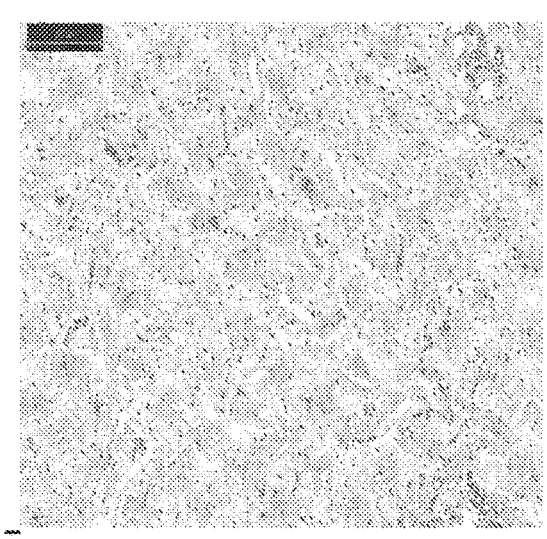

FIG. 11A illustrates histopathological sections colored by Masson's trichrome staining the tissue treated with the said 8% w/w gelatin crosslinked foam scaffold biomaterial at 30 days post injection. The results in FIG. 11A demonstrate the development of new, organized collagen fibers at the treated site. The new collagen is stained blue. FIG. 11B illustrates hematoxylin and eosin staining of the tissue, demonstrating limited presence of macrophages and giant cells post injection. No remnants of material are visible providing overall good biocompatibility outcome.

Example 14: Scar Prevention Using a Biodegradable Crosslinked Gelatin Foam

The following gelatin refers to Gelita 275 bloom, type A porcine gelatin (Gelita, Sioux City) medical grade low endotoxin, jet milled by Superfine Ltd to particle size of range: d(0.1)=4.24 μm, d(0.5)=16.61 μm, d(0.9)=31.51 μm. The following mTG refers to ACTIVA WM, powder with an activity level of 100 U/gm (Ajinomoto, Tokyo). The mTG contains 1% enzyme and 99% maltodextrin. Gelatin and mTG micronized powders were sterilized using gamma radiation 9.38 KGray (Sorvan, Israel). Gelatin: mTG ratio was 1 U mTG/10 mg gelatin. Dilution was 16.6% (w/w) of gelatin.

One 90 kg Large White crossed with Red Duroc swine, 10-months old, was used for the study. The animal was anesthetized, and seven surgical cuts were made on each of the left and right lateral side of the back of the animal. The left lateral side was used for clinical observation and the right lateral side for histological analysis. An ovoid piece of skin was removed. Using electrocautery, thermal damage to the wound beds was added to augment trauma and possible scarring. Prior to any intervention, one suture was placed in the middle of the cut to approximate the cut edges. Two additional sutures were placed roughly 1 cm above and beneath the middle of the cut. The sutures were placed such that 1-2 mm wound opening was visible and the sutures would not be too tightly closed.

The table below describes the wounds and treatment regimen.

It was shown that treating an open wound with a cross linkable gelatin foam at days 3-20 after surgery is beneficial in preventing scar formation. It was also shown that treating a wound at day 0 with the foam is not beneficial.

FIGS. 7A-7D illustrate the scars formed after 150 days post wound formation from Groups 1, 4, 6, and 7, respectively.

Example 16: Mixing of Crosslinked Gelatin Composition with Hyaluronic Acid (HA) without Losing Material Stability In Vivo The following gelatin refers to Gelita 275 bloom, type A porcine gelatin (Gelita, Sioux City) medical grade low endotoxin, jet milled by Superfine Ltd to particle size of range: d(0.1)=4.24 μm, d(0.5)=16.61 μm, d(0.9)=31.51 μm. The following mTG refers to ACTIVA WM, powder with an activity level of 100 U/gm (Ajinomoto, Tokyo). The mTG contains 1% enzyme and 99% maltodextrin. Micronized gelatin powder was screened (cut off larger particles) to reduce the size of gelatin particles and narrow the particle distribution range using a 100 micron mesh. Gelatin and mTG micronized powders were sterilized using gamma radiation 9.38 KGray (Sorvan, Israel).

One 90 kg Large White crossed with Red Duroc swine, 10-months old, was used for the study. The animal was anesthetized and an injection of the tested compositions (1.5 mL dilution) was tested for collagen production corresponding to 8% gelatin % w/w with 1 U mTG/10 mg gelatin. Prior to injection of the compound, 1 ml of hyaluronic acid (Belotero soft), was added to the syringe and mixed again. The material was injected into the hypodermis using a 21-gauge needle.

Figure 12:
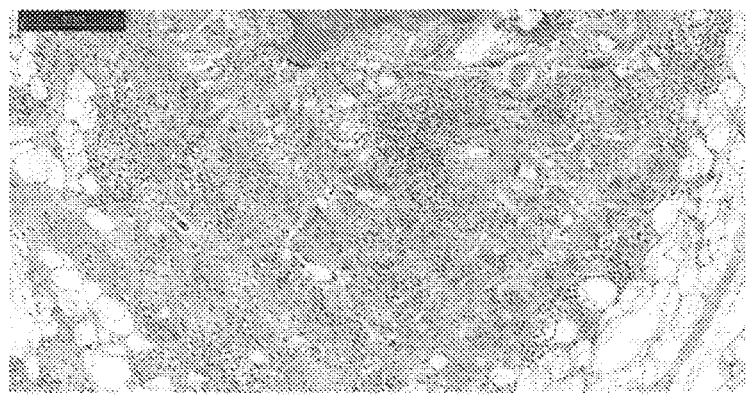
FIG. 12 is a photograph of a composition of the present inventions according to some embodiment of the present invention.
Figure 13A:
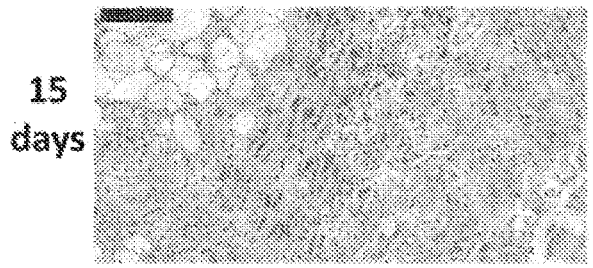
FIGS. 13A-D are photographs of compositions of the present invention according to some embodiments of the present invention.
Figure 13B:
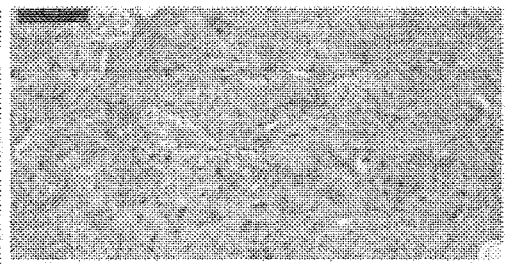
Figure 13C:
Figure 13D:
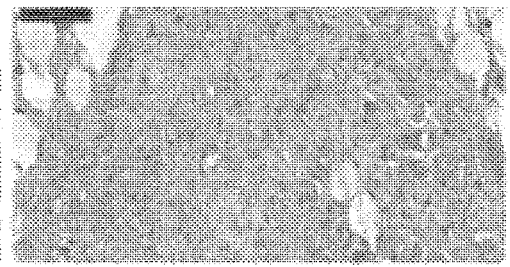

Results:

FIG. 12 illustrates histopathological sections hematoxylin and eosin staining of the tissue, demonstrating the presence of macrophages and giant cells post injection. Remnants of

|  | 1 Side closer to legs | 2 | 3 | 4 | 5 | 6 | 7 Side closer to head |
|---|---|---|---|---|---|---|---|
| Sutures | Add sutures to reduce tensile forces as much as possible* | No more sutures will be placed. only steri-strips will be used | Add sutures to reduce tensile forces as much as possible* | Add sutures to reduce tensile forces as much as possible* | Add sutures to reduce tensile forces as much as possible* | Add sutures to reduce tensile forces as much as possible* | Add sutures to reduce tensile forces as much as possible* |
| Injection time | Day 0 | Day 0 | Day 3 | Day 3 | Day 15-20 | Day 15-20 | No |
| Application Technique** | The material is placed in the surgical wound | The material is placed in the surgical wound | injected with cannula into the fat layer beneath the wound bed. | injected to the wound bed beneath the clot directly. | injected with cannula into the fat layer beneath the wound bed. | injected to the wound bed beneath the clot directly. | No |
| Effect of the gelatin in healing process | Inflammatory period with stitches | Inflammatory period without stitches | proliferative phase | proliferative phase | remodeling | remodeling phase | Control |

Results:

All lesions were evaluated blindly by a dermatologist expert in scar treatments. According to his observations, Groups 3-6 demonstrated significantly superior macroscopic outcomes in comparison to the control (Group 7) and to early phase injections (Groups 1 and 2).

material are visible, providing overall good biocompatibility outcome and showing that the material can be injected with hyaluronic acid without compromising the crosslinking of the gelatin by the pH affected enzyme.

Conclusions: Gelatin crosslinked compositions by microbial transglutaminase can be co-injected with other popular dermal fillers made of HA.

Example 17: Pro Collagen Type I Staining of Crosslinked Gelatin 150-Days Follow Up In Vivo Pig Model The following gelatin refers to Gelita 275 bloom, type A porcine gelatin (Gelita, Sioux City) medical grade low endotoxin, jet milled by Superfine Ltd to particle size of range: $d(0.1)=4.24$ µm, $d(0.5)=16.61$ µm, $d(0.9)=31.51$ µm. The following mTG refers to ACTIVA WM, powder with an activity level of 100 U/gm (Ajinomoto, Tokyo). The mTG contains 1% enzyme and 99% maltodextrin. Micronized gelatin powder was screened (cut off larger particles) to reduce the size of gelatin particles and narrow the particle distribution range using a 100-micron mesh. Gelatin and mTG micronized powders were sterilized using gamma radiation 9.38 KGray (Sorvan, Israel).

One 90 kg Large White crossed with Red Duroc swine, 10-months old, was used for the study. The animal was anesthetized and an injection of the tested compositions (1.5 mL dilution) was tested for collagen production corresponding to 12.5% gelatin % w/w with 1 U mTG/10 mg gelatin. Using a 21-gauge needle the material was injected to the hypodermis, in a 5×5 cm area. Biopsy were taken at 15 days, 30 days, 90 days, and 150 days post injection and stained with Pro collagen type I antibody abcam 64409.

Results: FIGS. 13A-D illustrate procollagen type I cells stained post injection. The procollagen type I cells are stained primarily at 15 days and 30 days post injection. Some staining is also visible at 90 days post injection. At 150 days post injection no staining is visible.

Conclusions: mTG crosslinked gelatin composition is able to induce the production of Collagen type I through production of Procollagen type I. The process peaks at around 30 days post injection and subsides by 150 days post injection.

Example 18: Crosslinked Gelatin and Purified mTG are Able to Induce Collagen Production The following gelatin refers to Gelita 275 bloom, type A porcine gelatin (Gelita, Sioux City) medical grade low endotoxin, jet milled by Superfine Ltd to particle size of range: $d(0.1)=4.24$ µm, $d(0.5)=16.61$ µm, $d(0.9)=31.51$ µm. The purified, E. coli grown recombinant, mTG was lyophilized from 25 mM Tris-Acetate pH 6.5, 300 mg/mL maltodextrin "Formula 204", or the purified mTG was lyophilized from 25 mM Tris-Acetate pH 6.5 "Formula 203". Native mTG refers to ACTIVA WM, powder with an activity level of 100 U/gm (Ajinomoto, Tokyo). Enzyme activity was measured using the hydroxymate assay kit purchased from Zedira GmbH Z009.

Micronized gelatin powder was screened (cut off larger particles) to reduce the size of gelatin particles and narrow the particle distribution range using a 100-micron mesh. Gelatin and mTG micronized powders were sterilized using gamma radiation 9.38 KGray (Sorvan, Israel).

One 90 kg Large White crossed with Red Duroc swine, 10-months old, was used for the study. The animal was anesthetized and an injection of the tested compositions (1.5 mL dilution) was tested for collagen production corresponding to 12.5 and 14% gelatin % w/w with 1 U mTG/10 mg gelatin. Using a 21-gauge needle the material was injected to the hypodermis, in a 5×5 cm area. Biopsies were taken at 30 days post injection.

Figure 14:
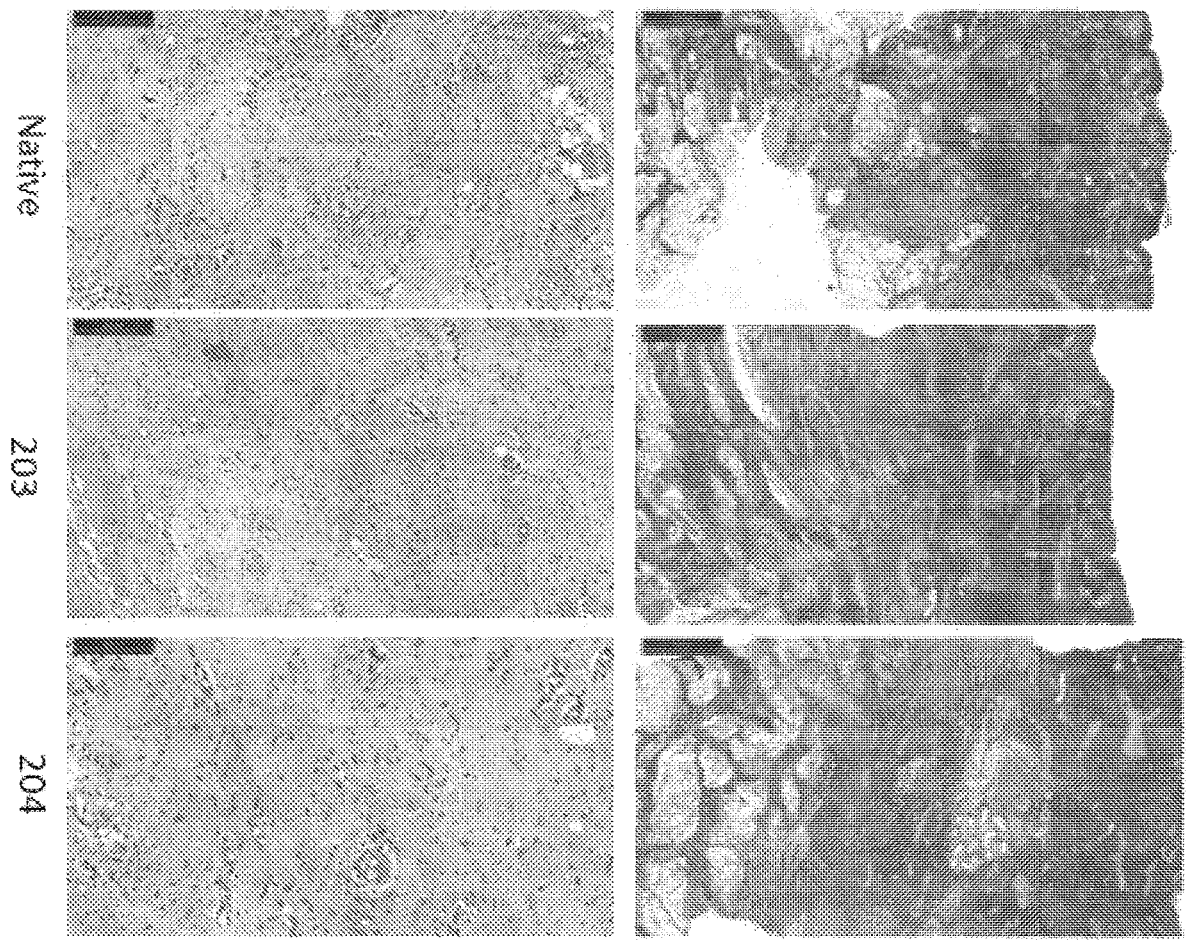
FIG. 14 are photographs of compositions of the present invention according to some embodiments of the present invention.

Results:
FIG. 14 illustrates Masson's trichrome staining (left) and hematoxylin and eosin staining (right) showing collagen production. The collagen production and immune response were comparable to the native formula containing the Activa-WM mTG.

Example 19: Mixing of Gelatin, mTG and Urea to Achieve Slower Gelation Time and Denser Implanted (Less Bubbles)

The following gelatin refers to Gelita 275 bloom, type A porcine gelatin (Gelita, Sioux City) medical grade low endotoxin, jet milled by Superfine Ltd to particle size of range: $d(0.1)=4.24$ µm, $d(0.5)=16.61$ µm, $d(0.9)=31.51$ µm. The following mTG refers to ACTIVA WM, powder with an activity level of 100 U/gm (Ajinomoto, Tokyo). The mTG contains 1% enzyme and 99% maltodextrin. Micronized gelatin powder was screened (cut off larger particles) to reduce the size of gelatin particles and narrow the particle distribution range using a 100 micron mesh. Gelatin and mTG micronized powders were sterilized using gamma radiation 9.38 KGray (Sorvan, Israel).

Urea was purchased from Sigma Aldrich.

Solutions containing PBS and either 0, 1, 2, 4 M urea were prepared.

1.5 ml of such solutions were loaded into syringes and connected with another syringe containing a mixture of 1:1 gelatin:mTG (total 500 mg) and mixed to create a foam.

Results:

After mixing, the foam was incubated at 37° C. and the gelation time (the time until the mixture is stable when flipped 90° degrees and is not flowing) and crosslinking time (the time until gelatin:mTG mixture is stable when inserted into a 55° C. water bath) were measured. As the concentration of urea increased, the gelation time and the crosslinking time increased (crosslinking was not achieved at 4M urea even after 30 minutes). The results show that adding urea can increase the injectability of the foam and improve surgeon working time (especially through thin needles). This is due to the delay of the physical gelation time of the hydrated gelatin and also inhibition of the enzymatic activity. It is also notable that the urea reduced the amount of bubbles in the foam and, in high doses, broke much of the foam into a confluent hydrogel.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A composition,
wherein the composition is a porous foam scaffold, wherein the pores of the foam scaffold are from 1 to 500 microns in diameter, the composition comprising:
a cross-linkable protein comprising at least one RGD (Arg-Gly-Asp) motif; and
a cross-linker which induces cross-linking of the cross-linkable protein, wherein the composition is absent a surfactant.

2. The composition of claim 1, wherein the cross-linkable protein is introduced into the composition as a micronized protein powder, having an average particle size between 5 to 200 microns.

3. The composition of claim 1, wherein the cross-linkable protein is selected from the group consisting of collagen and gelatin.

4. The composition of claim 3, wherein the cross-linkable gelatin is present in the composition in the range of 0.5% w/w to 25% w/w.

5. The composition of claim 1, wherein the cross-linker is transglutaminase.

6. The composition of claim 1, wherein the cross-linker is purified transglutaminase.

7. The composition of claim 1, wherein the cross-linker is microbial transglutaminase.

8. The composition of claim 1, wherein the composition is formed in situ in a patient at a site where the patient is in need of treatment of a skin defect.

9. The composition of claim 1, wherein the composition is formed prior to introducing the composition into a patient at a site where the patient is in need of treatment of a skin defect.

10. The composition of claim 1, wherein the composition is formed prior to introducing the composition into a patient at a site where the patient is in need of skin collagen regeneration.

11. The composition of claim 1, having a sufficient amount of the cross-linkable protein, so that when the porous scaffold is formed, the formed porous scaffold results in a Young's modulus of about 0.5-10 KPa.

12. The composition of claim 1, having a sufficient amount of the cross-linkable protein, so that when the porous scaffold is formed, the formed porous scaffold has an elongation that is less than 5 times its original length.

13. The composition of claim 1, having a sufficient amount of the cross-linker, so that when the porous scaffold is formed, the formed porous scaffold results in a Young's modulus of about 0.5-10 KPa.

14. The composition of claim 1, having a sufficient amount of the cross-linker, so that when the porous scaffold is formed, the formed porous scaffold has an elongation that is less than 5 times its original length.

15. The composition of claim 3, wherein the cross-linkable protein comprises gelatin of 200 to 300 bloom.

16. The composition of claim 3, wherein the gelatin is a recombinant gelatin.

17. The composition of claim 1, wherein the cross-linker is recombinant transglutaminase.

* * * * *